United States Patent
Klein et al.

(10) Patent No.: US 11,513,122 B2
(45) Date of Patent: Nov. 29, 2022

(54) PREDICTING RESPONSE TO PD-1 AXIS INHIBITORS

(71) Applicant: Hoffmann-La Roche Inc., Little Falls, NJ (US)

(72) Inventors: Christian Klein, Schlieren (CH); Maud Léa Mayoux, Schlieren (CH); Andreas Roller, Basel (CH); Wei Xu, Schlieren (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 367 days.

(21) Appl. No.: 16/362,940

(22) Filed: Mar. 25, 2019

(65) Prior Publication Data

US 2019/0346444 A1 Nov. 14, 2019

Related U.S. Application Data

(63) Continuation of application No. PCT/EP2017/074150, filed on Sep. 25, 2017.

(30) Foreign Application Priority Data

Sep. 26, 2016 (EP) .................................... 16190591
Apr. 18, 2017 (EP) .................................... 17166789

(51) Int. Cl.
*G01N 33/563* (2006.01)
*G01N 33/574* (2006.01)

(52) U.S. Cl.
CPC ..... *G01N 33/57407* (2013.01); *G01N 33/563* (2013.01)

(58) Field of Classification Search
CPC ....................... G01N 33/57407; G01N 33/563
USPC ...................................................... 424/133.1
See application file for complete search history.

(56) References Cited

U.S. PATENT DOCUMENTS

| 2013/0034559 A1 | 2/2013 | Queva et al. |
| 2015/0071910 A1 | 3/2015 | Kowanetz et al. |

FOREIGN PATENT DOCUMENTS

| WO | 2006/121168 A1 | 11/2006 |
| WO | 2007/005874 A2 | 1/2007 |
| WO | 2009/114335 A2 | 9/2009 |
| WO | 2010/027827 A2 | 3/2010 |
| WO | 2010/027827 A3 | 3/2010 |
| WO | 2010/077634 A1 | 7/2010 |
| WO | 2011/066342 A2 | 6/2011 |
| WO | 2011/066389 A1 | 6/2011 |
| WO | 2016/049641 A1 | 3/2016 |

OTHER PUBLICATIONS

Liu et al (Cell 165:535-550 (Apr. 21, 2016)).*
Mayoux et al (Euro. J. Imunol. 48, Suppl. 1, pp. 22-23, ABstract, Meeting Jun. 10, 2018-Jun. 14, 2018).*
Mayoux et al (Sci Transl. Med. 12:1-11 (Mar. 11, 2020)).*
Vajda et al., "Progress toward improved understanding of antibody maturation," Current Opinion in Structural Biology, 67 pp. 226-231 (2021).*
Marks et al., "How repertoire data are changing antibody science," J. Biol. Chem. 295(29) 9823-9837 (2020).*
Akbar et al., Cell Reports 34, 108856, Mar. 16, 2021).*
Lo et al., "Conformational epitope matching and prediction based on protein surface spiral features," BMC Genomics vol. 22, Article No. 116 (2021).*
Beatty et al., "CD40 agonists alter tumor stroma and show efficacy against pancreatic carcinoma in mice and humans" Science 331:1612-1616 (2011).
Brahmer et al., "Nivolumab versus Docetaxel in Advanced Squamous-Cell Non-Small-Cell Lung Cancer" The New England Journal of Medicine 373(2):123-135 ( 2015).
Brown et al., "Blockade of programmed death-1 ligands on dendritic cells enhances T cell activation and cytokine production" J Immunol. 170(3):1257-1266 ( 2003).
Butte et al., "Programmed Death-1 Ligand 1 Interacts Specifically with the B7-1 Costimulatory Molecule to Inhibit T Cell Responses" Immunity 27:111-122 ( 2007).
CAS Registry Database, 1422185-06-5 pp. 1 Jul. 3, 2012.
Dhodapkar et al., "Antigen-Specific Inhibition of Effector T Cell Function in Humans after Injection of Immature Dendritic Cells" The Journal of Experimental Medicine 193:233-238 ( 2001).
Dong et al., "B7-H1, a third member of the B7 family, co-stimulates T-cell proliferation and interleukin-10 secretion" Nature Medicine 5(12):1365-1369 (1999).
Gorgun et al., "Tumor-promoting immune-suppressive myeloid-derived suppressor cells in the multiple myeloma microenvironment in humans" Blood 121:2975-2987 ( 2013).
Herbst et al., "Predictive correlates of response to the anti-PD-L1 antibody MPDL3280A in cancer patients" Nature 515(7528):563-567 ( 2014).
International Preliminary Report on Patentability (IPRP) for PCT/EP2017/074150 dated Mar. 26, 2019.
International Search Report for PCT/EP2017/074150 dated Dec. 13, 2017.
Ishida et al., "Induced expression of PD-1, a novel member of the immunoglobulin gene superfamily, upon programmed cell death" EMBO J 11(11):3887-3895 ( 1992).
Jonuleit et al., "Dendritic cells as a tool to induce anergic and regulatory T cells" Trends in Immunology 22(7):394-400 ( 2011).
Karyampudi et al., "PD-1 Blunts the Function of Ovarian Tumor—Infiltrating Dendritic Cells by Inactivating NF-κB" Cancer Research 76:239-250 ( 2016).
Kazandjian et al., "FDA Approval Summary: Nivolumab for the Treatment of Metastatic Non-Small Cell Lung Cancer With Progression On or After Platinum-Based Chemotherapy" The Oncologist 21(5):634-642 ( 2016).
Keir et al., "PD-1 and its ligands in tolerance and immunity" Annu. Rev. Immunol. 26:677-704 ( 2008).

(Continued)

*Primary Examiner* — Lynn A Bristol

(57) ABSTRACT

The invention is concerned with a method of predicting response to a PD-1 axis inhibitor such as anti-PD-L1 antibody by determining the abundance of dendritic cells (DCs) in a tumor tissue sample. The abundance of DCs characterized by enhanced expressions of XCR1, IRF8, BATF3 and FLT3 predicts clinical response to the PD-L1 blockade 5 treatment.

3 Claims, 13 Drawing Sheets

Specification includes a Sequence Listing.

(56) References Cited

OTHER PUBLICATIONS

Krempski et al., "Tumor-infiltrating programmed death receptor-1+ dendritic cells mediate immune suppression in ovarian cancer" Journal of Immunology 186:6905-6913 ( 2011).

Kwang Chae et al., "Biomarkers for PD-1/PD-L1 Blockade Therapy in NoneSmall-cell Lung Cancer: Is PD-L1 Expression a Good Marker for Patient Selection?" Clinical Lung Cancer 17(5):350-361 ( 2016).

Li et al., "Comprehensive analyses of tumor immunity: implications for cancer immunotherapy", Genome Biology 17(174):1-16 ( 2016).

Nishimura et al., "Development of lupus-like autoimmune diseases by disruption of the PD-1 gene encoding an ITIM motif-carrying immunoreceptor" Immunity 11(2):141-51 (1999).

Park et al., "Negative role of inducible PD-1 on survival of activated dendritic cells" Journal of Leukocyte Biology 95:621-629 ( 2014).

Sanchez-Paulete et al., "Cancer Immunotherapy with Immunomodulatory Anti-CD137 and Anti-PD-1 Monoclonal Antibodies Requires BATF3-Dependent Dendritic Cells" Cancer Discovery 6(1):71-79 ( 2016).

Scarlett et al., "Ovarian cancer progression is controlled by phenotypic changes in dendritic cells." The Journal of Experimental Medicine 209(3):495-506 ( 2012).

Sharma et al., "Immune checkpoint targeting in cancer therapy: toward combination strategies with curative potential" Cell 161:205-214 ( 2015).

Steinman et al., "Tolerogenic dendritic cells" Annu. Rev. Immunol. 21:685-711 ( 2003).

Weide et al., "Immunologic Correlates in the Course of Treatment With Immunomodulating Antibodies" Seminars in Oncology 42(3):448-458 ( 2015).

Yao et al., "PD-1 on dendritic cells impedes innate immunity against bacterial infection." Blood 113:5811-5818 ( 2009).

Zou et al., "PD-L1 (B7-H1) and PD-1 pathway blockade for cancer therapy: Mechanisms, response biomarkers, and combinations" Science Translational Medicine 8(328 328rv4):1-14 ( 2016).

Cancer and Immunity "Anti-tumor immune response" Sakaguchi, et al., 1 edition, Tokyo, Japan:Nanzan Do Hall,:164-176 (Oct. 15, 2015).

Terasaki, "New Horizons in Pharmaceutics; Importance of Protein Quantification" Pharmaceutics 74(3):171 ( 2014).

\* cited by examiner

|  | Total | CR | PR | SD | PD | UE |
|---|---|---|---|---|---|---|
|  | 56 | 1 | 5 | 26 | 21 | 3 |
| % |  | 1.8 | 8.9 | 46.4 | 37.5 | 5.4 |

CR: Complete Response; PR: Partial Response; SD: Stable Disease;
PD: Progressive Disease; UE: Unevaluable

FIG. 7

| Gene | Hazard Ratio (HR) (95% cI) | p value (COX HR) | Median OS (-) | Median OS (+) | p value (Kaplan Meier Curve) |
|---|---|---|---|---|---|
| XCR1 | 0.35 (0.14 - 0.90) | 0.03 | 19.0 | n.r. | 0.0034 |
| IRF8 | 0.53 (0.23 - 1.19) | 0.12 | 16.6 | n.r. | 0.01 |
| BATF3 | 0.49 (0.20 - 1.17) | 0.11 | 19.0 | 35.4 | 0.12 |
| FLT3 | 0.69 (0.32 - 1.53) | 0.37 | 20.6 | 36.2 | 0.15 |

FIG. 9

PREDICTING RESPONSE TO PD-1 AXIS INHIBITORS

CROSS REFERENCE TO RELATED APPLICATIONS

This application is a continuation of International Application No. PCT/EP2017/074150 having an International Filing Date of 25 Sep. 2017, claiming priority to application numbers EP 16190591.4 filed 26 Sep. 2016 and EP 17166789.2 filed 18 Apr. 2017, each of which are incorporated herein by reference in its entirety.

SEQUENCE LISTING

This application contains a Sequence Listing which has been submitted electronically in ASCII format and is hereby incorporated by reference in its entirety. Said ASCII copy, created on Mar. 5, 2019, is named P33856-US_Sequence_Listing.txt and is 9,430 bytes in size.

FIELD OF THE INVENTION

The present invention relates to a biomarker for predicting response of a patient with a cancer to a PD-1 axis inhibitor such as an anti-PD-L1 antibody. Provided herein is a method of identifying a cancer patient responsive to a PD-1 axis inhibitor by determining the abundance of dendritic cells (DCs) in a tumor tissue sample.

BACKGROUND OF THE INVENTION

Myeloid cells including DCs and macrophages are crucial in initiating adaptive immune response via priming of naive T cells to educate and generate effector cells. DCs, the professional antigen-presenting cells (APC), are bone marrow-derived cells that populate all lymphoid organs as well as nearly all non-lymphoid organs. Pathogen-sensed mature DCs in the periphery express high levels of MHC (class I and II) and costimulatory molecules, and are able to migrate to the secondary lymphoid organs to stimulate naïve T cells to induce adaptive immunity.

On the other hand, many myeloid cell subsets are able to infiltrate the tumor microenvironment, and depending on the activation status, they provide tumor escaping mechanism via immune-suppression or direct tumoricidal activities. Various markers can reflect the state of DCs and macrophages activation, one example of activating receptor is the CD40 protein. Antibodies agonizing the CD40 receptor have shown anti-tumor effects in both preclinical and clinical settings by activating the DCs to induce T cell infiltration into the tumor and by polarizing macrophages to kill tumors (Beatty et al., 2011, Science, 331: 1612-6). On the contrary, Myeloid-derived suppressor cells (MDSC) have been identified to play a negative role in the tumor microenvironment by promoting immune-suppressive responses in several solid cancers as shown in human melanoma (Gorgun et al., 2013, Blood, 121: 2975-87). Therefore a more comprehensive understanding of how the immunosuppressive milieu develops and persists is critical to guide the success of full power new immunotherapies.

PD-1 is an immunoglobulin superfamily member discovered on 1992 as a gene up-regulated in T cell hybridoma undergoing cell death (Ishida et al., 1992, EMBO J, 11: 3887-95). PD-1 is mainly found on activated T, B and myeloid cells. The important negative regulatory function of PD-1 was revealed by autoimmune-prone phenotype of Pdcd1-/- mice in 1999 (Nishimura et al., 1999, Immunity, 11: 141-51). In 1999 PD-L1 (B7-H1), the first ligand of PD-1, was identified (Dong et al., 1999, Nat Med, 5: 1365-9), followed by PD-L2 (B7-DC) in 2001 (Latchman et al., 2001, Nat Immunol, 2: 261-8). Another costimulatory molecule, the CD80 (B7-1) interacts specifically with PD-L1 (Butte et al., 2007, Immunity, 27: 111-22) as well. PD-1 contains two immunoreceptor tyrosine-based motifs that are phosphorylated upon receptor engagement and recruit Src homology 2-domain-containing tyrosine phosphatase 2. The PD-1:PD-L1 pathway inhibits T cell proliferation by reducing the production of IL-2 and restricts the number of T cells that gain entry into the cell cycle as well as their subsequent division rate. Up-regulation of PD-L1 expression was described in several human tumors types, which hijacks the PD-L1 to interact with PD-1 on T cells and suppress effector function. These findings led to the successful clinical application of PD-1 blockade in treating solid tumors (Sharma et al., 2015, Cell, 161: 205-14). Nevertheless, so far only a minor subset of patients (<30%) benefit from such a therapy, with as-yet unknown mechanisms (Zou et al., 2016, Sci Transl Med, 8: 328rv4).

Accordingly, there is a need for methods for determining which patients respond particularly well to a therapy with a PD-1 axis inhibitor such as an anti-PD-L1 antibody that inhibits the binding of PD-L1 to PD-1.

SUMMARY OF THE INVENTION

Despite intensive research on the role of PD-1 in lymphocytes, little has been studied to unravel the molecular regulation of PD-1/PD-L1 pathway on myeloid cells, particularly on DCs, and the significance of this pathway blockade in regulating tumor immunity. Depending on the activating signals, certain subpopulations of DCs are able to suppress immune responses by establishing and maintaining T cell tolerance (Dhodapkar et al., 2001, J Exp Med, 193: 233-8; Steinman et al., 2003, Annu Rev Immunol, 21: 685-711; Jonuleit et al., 2001., Trends Immunol, 22: 394-400). Immunosuppressive DCs were found in the tumor microenvironment (Scarlett et al., 2012., J Exp Med, 209: 495-506). Interestingly, tumor-infiltrating DCs became PD-1 positive over the course of ovarian cancer progression (Krempski et al., 2011., J Immunol, 186: 6905-13), and it seems likely that PD-1 blocked Nuclear Factor-kappa B-dependent activation to render the DCs immunosuppressive (Karyampudi et al., 2016, Cancer Res, 76: 239-50). Earlier studies have indicated that blocking PD-L1 on human DCs in vitro enhanced T cell immunity (Brown et al., 2003, J Immunol, 170: 1257-66). It was suggested that PD-1 negatively regulates murine DCs in vivo (Krempski et al. 2011; Park et al., 2014, J Leukoc Biol, 95: 621-9; Yao et al., 2009, Blood, 113: 5811-8). Given that PD-L1 binds to both CD80 and PD-1 (Keir et al., 2008, Annu Rev Immunol, 26: 677-704), and DCs express all these three receptors/ligands simultaneously, the inventors hypothesized that PD-1/PD-L1 is regulated in a controlled manner, thus immunotherapies targeting this pathway could hold a yet underappreciated mechanism of actions by modulating DCs function and/or other myeloid cell subset that influence the downstream T cell lineage development.

Provided herein is evidence that DCs are the primary targets of PD-L1 blockade enabling enhanced anti-tumor immunity. It is shown that human DCs express both PD-1 and PD-L1, and the PD-1 is negatively regulated upon activation by DCs. Further, PD-L1 blockade directly activate DCs, rendering them acquire enhanced capacity to activate T cells, both in human in vitro settings and in tumor-bearing mice. Depleting DCs in mice where tumor has been established showed a compromised response to PD-L1 blockade treatment, suggesting a direct contribution of DCs to PD-L1 blockade-mediated anti-tumor immunity. Moreover, the analysis of tumor biopsy at baseline from patients with renal cell carcinoma who received treatment with an anti-PD-L1 antibody, atezolizumab, and showed that patients with higher expressions of genes related to development and function of DCs had a significant survival advantage as compared to those with lower expressions. Thus, the data support that PD-L1 blockade directly targets DCs to enhance anti-tumor immunity. The abundance of functional DCs in tumor tissue is predictor of a better clinical outcome in response to a therapy with a PD-1 axis inhibitor such as PD-L1 blockade treatment.

It is further demonstrated herein that, upon maturation of DCs, PD-1 expression is downregulated. However, PD-L1 expression increases, which leads to binding of PD-L1 to CD80 on the surface of DCs, sequestering CD80 and preventing binding of CD80 to CD28 for co-stimulation on T cells. Administration of PD-L1 antibodies relieves the CD80 sequestration, enabling further co-stimulation of anti-cancer T cells through CD80/CD28 interaction. This represents the first demonstration of how the PD-L1/PD-1 pathway biologically inhibits DCs in tumor, and functions as an immune checkpoint in anti-cancer T cell priming and activation.

Provided herein therefore are a method of predicting clinical response to a PD-1 axis inhibitor in a patient with cancer and a pharmaceutical composition comprising a PD1 axis inhibitor for use in treatment of a patient with cancer who is likely to respond to a PD-1 axis inhibitor.

The following numbered paragraphs (para.) define some embodiments of the present invention.

1. An in vitro method of identifying a patient with cancer who is responsive to a therapy comprising an effective amount of a PD-1 axis inhibitor, the method comprising determining the abundance of dendritic cells (DCs) in a tumor tissue sample obtained from a patient with cancer.

2. The method of para 1, wherein the abundance of DCs is characterized by an expression level of one or more genes selected from the group consisting of XCR1, IRF8, BATF3 and FLT3.

3. The method of para. 2, wherein the method further comprises a step of comparing the expression level of the one or more genes to a reference level, whereby an increased expression level is indicative of response to a therapy comprising a PD-1 axis inhibitor.

4. The method of para. 2 or 3, wherein the expression level is detected in the sample by protein expression.

5. The method of para. 2 or 3, wherein the expression level is detected in the sample by mRNA expression.

6. The method of any one of para. 2 to 5, wherein the expression level is detected using a method selected from the group consisting of FACS, Western blot, ELISA, immunoprecipitation, immunohistochemistry, immunofluorescence, radioimmunoas say, immunodetection methods, mass spectrometery, HPLC, qPCR, RT-qPCR, multiplex qPCR or RT-qPCR, RNA-seq, microarray analysis, nanostring, SAGE, MassARRAY technique, and FISH, and combinations thereof.

7. The method of any one of para. 1 to 6, wherein the cancer is selected from the group consisting of non-small cell lung cancer, small cell lung cancer, renal cell cancer, colorectal cancer, ovarian cancer, breast cancer, pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, leukemia, lymphomas, myelomas, mycoses fungoids, merkel cell cancer, and other hematologic malignancies.

8. The method of any one of para. 1 to 7, wherein the therapy includes a PD-1 axis inhibitor as monotherapy.

9. The method of any one of para. 1 to 7, wherein the therapy further comprises an effective amount of a second agent selected from the group consisting of cytotoxic agent, a chemotherapeutic agent, a growth inhibitory agent, a radiation therapy agent, and anti-angiogenic agent, and combinations thereof.

10. The method of any one of para. 1 to 9, wherein the PD-1 axis inhibitor is a PD-1 binding antagonist.

11. The method of para. 10, wherein the PD-1 binding antagonist inhibits the binding of PD-1 to PD-L1.

12. The method of para. 10 or 11, wherein the PD-1 binding antagonist is an anti-PD-1 antibody.

13. The method of any one of para. 1 to 9, wherein the PD-1 axis inhibitor is a PD-L1 binding antagonist.

14. The method of para. 13, wherein the PD-L1 binding antagonist inhibits the binding of PD-L1 to PD-1.

15. The method of para. 13 or 14, wherein PD-L1 binding antagonist is an anti-PD-L1 antibody.

16. The method of para. 15, wherein the anti-PD-L1 antibody is an antibody fragment selected from the group consisting of Fab, Fab'-SH, Fv, scFv, and (Fab')2 fragments.

17. The method of para. 15 or 16, wherein the anti-PD-L1 antibody is selected from the group consisting of YW243.55.570, MPDL3280A, MDX-1105, and MEDI4736.

18. The method of any one of para. 1 to 17, wherein the tumor tissue sample is a sample obtained from the patient prior to the therapy with a PD-1 axis inhibitor.

19. A pharmaceutical composition comprising a PD-1 axis inhibitor for use in the treatment of a patient with cancer, wherein the patient is determined to be responsive to a therapy comprising an effective amount of a PD-1 axis inhibitor in accordance with the method of any one of para. 1 to 18.

In some embodiments, the present invention relates to a method of determining whether a patient with cancer is more suitably treated by a therapy comprising an effective amount of a PD-1 axis inhibitor, the method comprising determining the abundance of DCs in a tumor tissue sample obtained from a patient with cancer.

In some embodiments, the present invention relates to a method of improving the treatment effect of a therapy comprising an effective amount of a PD-1 axis inhibitor in a patient with cancer, the method comprising determining the abundance of DCs in a tumor tissue sample obtained from a patient with cancer.

In some embodiments, the present invention relates to a method of treating a patient with cancer. The method comprises administering to a patient with cancer a therapy comprising an effective amount of a PD-1 axis inhibitor, the method comprising determining the abundance of DCs in a tumor tissue sample obtained from the patient.

These and other embodiments are further described in the detailed description below.

BRIEF DESCRIPTION OF THE FIGURES

FIG. 7 summarizes clinical response to atezolizumab in patients with renal cell carcinoma.

FIG. 9 summarizes a list of genes related to DCs and the correlative response to the Kaplan-Meier survival curve.

DETAILED DESCRIPTION OF THE EMBODIMENTS

Definitions

Figure 1A:
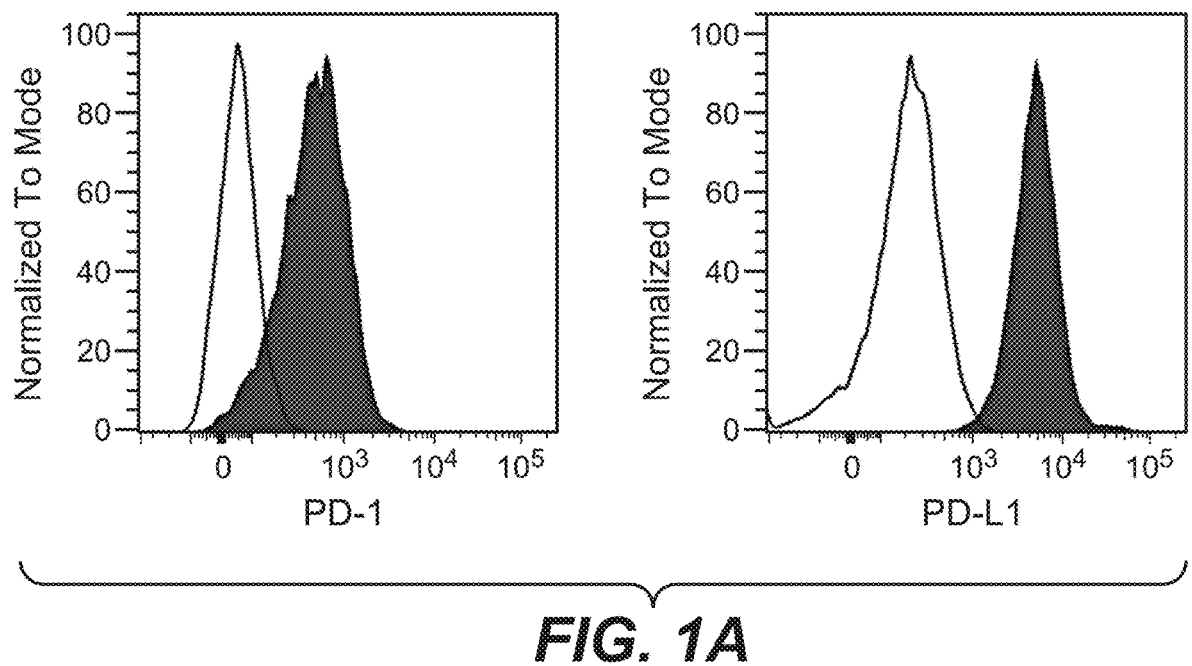
FIGS. 1A-1B show the immunostaining of PD-1 and PD-L1 expression on human DCs. In vitro-generated DCs express both PD-1 and PD-L1 (FIG. 1A), and the expression profile of PD-1 and PD-L1 is negatively correlated (FIG. 1B).

The term "PD-1 axis inhibitor" is a molecule that inhibits the interaction of a PD-1 axis binding partner with either one or more of its binding partner, so as to remove T-cell dysfunction resulting from signaling on the PD-1 signaling axis—with a result being to restore or enhance T-cell function, e.g., proliferation, cytokine production, target cell killing. As used herein, a PD-1 axis inhibitor includes a PD-1 binding antagonist and a PD-L1 binding antagonist.

The term "PD-1 binding antagonist" is a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional, e.g. enhancing effector responses to antigen recognition. In some embodiments, the PD-1 binding antagonist is an anti-PD-1 antibody. In a specific aspect, a PD-1 binding antagonist is MDX-1106 described herein. In another specific aspect, a PD-1 binding antagonist is Merck 3745 described herein.

The term "PD-L1 binding antagonist" is a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1 and B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional, e.g. enhancing effector responses to antigen recognition. In some embodiments, a PD-L1 binding antagonist is an anti-PD-L1 antibody. In a specific aspect, an anti-PD-L1 antibody is YW243.55.570 described herein. In another specific aspect, an anti-PD-L1 antibody is MDX-1105 described herein. In still another specific aspect, an anti-PD-L1 antibody is MPDL3280A described herein.

The term "antibody" herein is used in the broadest sense and encompasses various antibody structures, including but not limited to monoclonal antibodies, polyclonal antibodies, multispecific antibodies, e.g., bispecific antibodies, and antibody fragments so long as they exhibit the desired antigen-binding activity.

The terms "anti-PD-L1 antibody" and "an antibody that binds to PD-L1" refer to an antibody that is capable of binding PD-L1 with sufficient affinity such that the antibody is useful as a diagnostic and/or therapeutic agent in targeting PD-L1. In one embodiment, the extent of binding of an anti-PD-L1 antibody to an unrelated, non-PD-L1 protein is less than about 10% of the binding of the antibody to PD-L1 as measured, e.g., by a radioimmunoassay (RIA). In certain embodiments, an anti-PD-L1 antibody binds to an epitope of PD-L1 that is conserved among PD-L1 from different species.

A "blocking" antibody or an "antagonist" antibody is one which inhibits or reduces biological activity of the antigen it binds. Preferred blocking antibodies or antagonist antibodies substantially or completely inhibit the biological activity of the antigen.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g., scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The terms "full length antibody," "intact antibody," and "whole antibody" are used herein interchangeably to refer to an antibody having a structure substantially similar to a native antibody structure or having heavy chains that contain an Fc region as defined herein.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "detection" includes any means of detecting, including direct and indirect detection.

The term "biomarker" as used herein refers to an indicator, e.g., predictive, diagnostic, and/or prognostic, which can be detected in a sample. The biomarker may serve as an indicator of a particular subtype of a disease or disorder (e.g., cancer) characterized by certain, molecular, pathological, histological, and/or clinical features. In some embodiments, a biomarker is a gene. Biomarkers include, but are not limited to, polynucleotides (e.g., DNA, and/or RNA), polynucleotide copy number alterations (e.g., DNA copy numbers), polypeptides, polypeptide and polynucleotide modifications (e.g. posttranslational modifications), carbohydrates, and/or glycolipid-based molecular markers.

The terms "biomarker signature," "signature," "biomarker expression signature," or "expression signature" are used interchangeably herein and refer to one or a combination of biomarkers whose expression is an indicator, e.g., predictive, diagnostic, and/or prognostic. The biomarker signature may serve as an indicator of a particular subtype of a disease or disorder (e.g., cancer) characterized by certain molecular, pathological, histological, and/or clinical features. In some embodiments, the biomarker signature is a "gene signature." The term "gene signature" is used interchangeably with "gene expression signature" and refers to one or a combination of polynucleotides whose expression is an indicator, e.g., predictive, diagnostic, and/or prognostic. In some embodiments, the biomarker signature is a "protein signature." The term "protein signature" is used interchangeably with "protein expression signature" and refers to one or a combination of polypeptides whose expression is an indicator, e.g., predictive, diagnostic, and/or prognostic.

The "amount" or "level" of a biomarker associated with an increased clinical benefit to an individual is a detectable level in a biological sample. These can be measured by methods known to one skilled in the art and also disclosed herein. The expression level or amount of biomarker assessed can be used to determine the response to the treatment.

The terms "level of expression" or "expression level" in general are used interchangeably and generally refer to the amount of a biomarker in a biological sample. "Expression" generally refers to the process by which information (e.g., gene-encoded and/or epigenetic) is converted into the structures present and operating in the cell. Therefore, as used herein, "expression" may refer to transcription into a polynucleotide, translation into a polypeptide, or even polynucleotide and/or polypeptide modifications (e.g., posttranslational modification of a polypeptide). Fragments of the transcribed polynucleotide, the translated polypeptide, or polynucleotide and/or polypeptide modifications (e.g., post-translational modification of a polypeptide) shall also be regarded as expressed whether they originate from a transcript generated by alternative splicing or a degraded transcript, or from a post-translational processing of the polypeptide, e.g., by proteolysis. "Expressed genes" include those that are transcribed into a polynucleotide as mRNA and then translated into a polypeptide, and also those that are transcribed into RNA but not translated into a polypeptide (for example, transfer and ribosomal RNAs).

The term "reference level" herein refers to a predetermined value. As a skilled person will appreciate the reference level is predetermined and set to meet the requirements in terms of e.g. specificity and/or sensitivity. These requirements can vary, e.g. from regulatory body to regulatory body. It may for example be that assay sensitivity or specificity, respectively, has to be set to certain limits, e.g. 80%, 90% or 95%. These requirements may also be defined in terms of positive or negative predictive values. Nonetheless, based on the teaching given in the present invention it will always be possible to arrive at the reference level meeting those requirements. In one embodiment the reference level is determined in healthy individuals. The reference value in one embodiment has been predetermined in the disease entity to which the patient belongs. In certain embodiments the reference level can e.g. be set to any percentage between 25% and 75% of the overall distribution of the values in a disease entity investigated. In other embodiments the reference level can e.g. be set to the median, tertiles or quartiles as determined from the overall distribution of the values in a disease entity investigated. In one embodiment the reference level is set to the median value as determined from the overall distribution of the values in a disease entity investigated.

In certain embodiments, the term "increase", "increased" or "above" refers to a level above the reference level.

"Amplification," as used herein generally refers to the process of producing multiple copies of a desired sequence. "Multiple copies" mean at least two copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

The term "multiplex-PCR" refers to a single PCR reaction carried out on nucleic acid obtained from a single source (e.g., an individual) using more than one primer set for the purpose of amplifying two or more DNA sequences in a single reaction.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, can be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with a 10 minute wash at 42° C. in 0.2×SSC (sodium chloride/sodium citrate) followed by a 10 minute high-stringency wash consisting of 0.1×SSC containing EDTA at 55° C.

"Moderately stringent conditions" can be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The technique of "polymerase chain reaction" or "PCR" as used herein generally refers to a procedure wherein minute amounts of a specific piece of nucleic acid, RNA and/or DNA, are amplified as described in U.S. Pat. No. 4,683,195 issued 28 Jul. 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., Cold Spring Harbor Symp. Quant. Biol., 51: 263 (1987); Erlich, ed., PCR Technology, (Stockton Press, N.Y., 1989). As used herein, PCR is considered to be one, but not the only, example of a nucleic acid polymerase reaction method for amplifying a nucleic acid test sample, comprising the use of a known nucleic acid (DNA or RNA) as a primer and utilizes a nucleic acid polymerase to amplify or generate a specific piece of nucleic acid or to amplify or generate a specific piece of nucleic acid which is complementary to a particular nucleic acid.

"Quantitative real time polymerase chain reaction" or "qRT-PCR" refers to a form of PCR wherein the amount of PCR product is measured at each step in a PCR reaction. This technique has been described in various publications including Cronin et al., Am. J. Pathol. 164(1):35-42 (2004); and Ma et al., Cancer Cell 5:607-616 (2004).

The term "microarray" refers to an ordered arrangement of hybridizable array elements, preferably polynucleotide probes, on a substrate.

The term "polynucleotide," when used in singular or plural, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The term "diagnosis" is used herein to refer to the identification or classification of a molecular or pathological state, disease or condition (e.g., cancer). For example, "diagnosis" may refer to identification of a particular type of cancer. "Diagnosis" may also refer to the classification of a particular subtype of cancer, e.g., by histopathological criteria, or by molecular features (e.g., a subtype characterized by expression of one or a combination of biomarkers (e.g., particular genes or proteins encoded by said genes)).

The term "sample," as used herein, refers to a composition that is obtained or derived from a subject and/or individual of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized. Samples include, but are not limited to, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebrospinal fluid, saliva, sputum, tears, perspiration, mucus, tumor lysates, and tissue culture medium, tissue extracts such as homogenized tissue, tumor tissue, cellular extracts, and combinations thereof.

By "tissue sample" or "cell sample" is meant a collection of similar cells obtained from a tissue of a subject or individual. The source of the tissue or cell sample may be solid tissue as from a fresh, frozen and/or preserved organ, tissue sample, biopsy, and/or aspirate; blood or any blood constituents such as plasma; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

A "reference sample", "reference cell", "reference tissue", "control sample", "control cell", or "control tissue", as used herein, refers to a sample, cell, tissue, standard, or level that is used for comparison purposes. In one embodiment, a reference sample, reference cell, reference tissue, control sample, control cell, or control tissue is obtained from a healthy and/or non-diseased part of the body (e.g., tissue or cells) of the same subject or individual. For example, healthy and/or non-diseased cells or tissue adjacent to the diseased cells or tissue (e.g., cells or tissue adjacent to a tumor). In another embodiment, a reference sample is obtained from an untreated tissue and/or cell of the body of the same subject or individual. In yet another embodiment, a reference sample, reference cell, reference tissue, control sample, control cell, or control tissue is obtained from a healthy and/or non-diseased part of the body (e.g., tissues or cells) of an individual who is not the subject or individual. In even another embodiment, a reference sample, reference cell, reference tissue, control sample, control cell, or control tissue is obtained from an untreated tissue and/or cell of the body of an individual who is not the subject or individual.

For the purposes herein a "section" of a tissue sample is meant a single part or piece of a tissue sample, e.g. a thin slice of tissue or cells cut from a tissue sample. It is understood that multiple sections of tissue samples may be taken and subjected to analysis, provided that it is understood that the same section of tissue sample may be analyzed at both morphological and molecular levels, or analyzed with respect to both polypeptides and polynucleotides.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of polypeptide analysis or protocol, one may use the results of the polypeptide expression analysis or protocol to determine whether a specific therapeutic regimen should be performed. With respect to the embodiment of polynucleotide analysis or protocol, one may use the results of the polynucleotide expression analysis or protocol to determine whether a specific therapeutic regimen should be performed.

"Individual response" or "response" can be assessed using any endpoint indicating a benefit to the individual, including, without limitation, (1) inhibition, to some extent, of disease progression (e.g., cancer progression), including slowing down and complete arrest; (2) a reduction in tumor size; (3) inhibition (i.e., reduction, slowing down or complete stopping) of cancer cell infiltration into adjacent peripheral organs and/or tissues; (4) inhibition (i.e. reduction, slowing down or complete stopping) of metastasis; (5) relief, to some extent, of one or more symptoms associated with the disease or disorder (e.g., cancer); (6) increase or extend in the length of survival, including overall survival and progression free survival; and/or (7) decreased mortality at a given point of time following treatment.

An "effective response" of a patient or a patient's "responsiveness" to treatment with a medicament and similar wording refers to the clinical or therapeutic benefit imparted to a patient at risk for, or suffering from, a disease or disorder, such as cancer. In one embodiment, such benefit includes any one or more of: extending survival (including overall survival and progression free survival); resulting in an objective response (including a complete response or a partial response); or improving signs or symptoms of cancer. In one embodiment, the presence of the biomarker is used to identify a patient who is more likely to respond to treatment with a medicament, relative to a patient that does not have the presence of the biomarker. In another embodiment, the presence of the biomarker is used to determine that a patient will have an increase likelihood of benefit from treatment with a medicament, relative to a patient that does not have the presence of the biomarker.

"Survival" refers to the patient remaining alive, and includes overall survival as well as progression free survival.

"Overall survival" refers to the patient remaining alive for a defined period of time, such as 1 year, 5 years, etc from the time of diagnosis or treatment.

"Progression free survival" refers to the patient remaining alive, without the cancer progressing or getting worse.

By "extending survival" is meant increasing overall or progression free survival in a treated patient relative to an untreated patient (i.e. relative to a patient not treated with the medicament), or relative to a patient who does not express a biomarker at the designated level, and/or relative to a patient treated with an approved anti-tumor agent. An objective response refers to a measurable response, including complete response (CR) or partial response (PR).

By complete response or "CR" is intended the disappearance of all signs of cancer in response to treatment. This does not always mean the cancer has been cured.

Partial response or "PR" refers to a decrease in the size of one or more tumors or lesions, or in the extent of cancer in the body, in response to treatment.

An "effective amount" of an agent refers to an amount effective, at dosages and for periods of time necessary, to achieve the desired therapeutic or prophylactic result.

A "therapeutically effective amount" refers to an amount of a therapeutic agent to treat or prevent a disease or disorder in a mammal. In the case of cancers, the therapeutically effective amount of the therapeutic agent may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The terms "cancer" and "cancerous" refer to or describe the physiological condition in mammals that is typically characterized by unregulated cell growth. Included in this definition are benign and malignant cancers. By "early stage cancer" or "early stage tumor" is meant a cancer that is not invasive or metastatic or is classified as a Stage 0, I, or II cancer. Examples of cancer include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g. epithelial squamous cell cancer), lung cancer including small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, merkel cell cancer, mycoses fungoids, testicular cancer, esophageal cancer, tumors of the biliary tract, as well as head and neck cancer and hematological malignancies. In some embodiments, the cancer is triple-negative metastatic breast cancer, including any histologically confirmed triple-negative (ER−, PR−, HER2−) adenocarcinoma of the breast with locally recurrent or metastatic disease (where the locally recurrent disease is not amenable to resection with curative intent).

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject., A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies are used to delay development of a disease or to slow the progression of a disease.

The term "anti-cancer therapy" refers to a therapy useful in treating cancer. Examples of anti-cancer therapeutic agents include, but are limited to, e.g., chemotherapeutic agents, growth inhibitory agents, cytotoxic agents, agents used in radiation therapy, anti-angiogenesis agents, apoptotic agents, anti-tubulin agents, and other agents to treat cancer, anti-CD20 antibodies, platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets PDGFR-beta, BlyS, APRIL, BCMA receptor(s), TRAIL/Apo2, and other bioactive and organic chemical agents, etc. Combinations thereof are also included in the invention.

The term "cytotoxic agent" as used herein refers to a substance that inhibits or prevents the function of cells and/or causes destruction of cells. The term is intended to include radioactive isotopes (e.g., At211, I131, I125, Y90, Re186, Re188, Sm153, Bi212, P32 and radioactive isotopes of Lu), chemotherapeutic agents e.g., methotrexate, adriamicin, *vinca* alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" refers to a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Nicolaou et al., Angew. Chem Intl. Ed. Engl., 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®)); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g., celecoxib or etoricoxib), proteosome inhibitor (e.g., PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "antihormonal agents" or "endocrine therapeutics" which act to regulate, reduce, block, or inhibit the effects of hormones that can promote the growth of cancer. They may be hormones themselves, including, but not limited to: antiestrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

A "growth inhibitory agent" when used herein refers to a compound or composition which inhibits growth of a cell (e.g., a cell whose growth is dependent upon PD-L1 expression either in vitro or in vivo). Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s).

By "reduce or inhibit" is meant the ability to cause an overall decrease of 20%, 30%, 40%, 50%, 60%, 70%, 75%, 80%, 85%, 90%, 95%, or greater. Reduce or inhibit can refer to the symptoms of the disorder being treated, the presence or size of metastases, or the size of the primary tumor.

It is understood that the singular form "a", "an", and "the" includes plural references unless indicated otherwise.

Dendritic Cell Markers

In the present invention, abundance of DCs in a tumor tissue sample obtained from a patient with cancer (i.e. tumor-infiltrating DCs), more preferably functional DCs with cross-presenting capacity, was found to be predictive of response to PD-1 axis inhibitors. Abundance of DCs can be determined by detecting expression levels of markers associated with development, activation or manuration of DCs with cross-presenting properties. Those markers include XCR1, IRF8, BATF3, FLT3. These markers may be considered separately, as individual markers, or in groups of two or more markers, as a cumulative expression of the markers, i.e. a cumulative DC gene score (DC score). The expression levels of two or more markers can be combined by any appropriate state of the art mathematical method to obtain a DC score. In one embodiment, a DC score can be obtained on the basis of expression levels of genes consisting of XCR1, IRF8, BATF3, and FLT3.

In one embodiment, the biomarker of the present invention is used for predicting response of patients with renal cell carcinoma to a PD-1 axis inhibitor such as an anti-PD-L1 antibody atezolizumab. In another embodiment, the biomarker of the present invention is used for predicting response of patients with non-small cell lung cancer (NSCLC) to a PD-1 axis inhibitor such as an anti-PD-L1 antibody atezolizumab. According to the embodiments of the present invention, the predictive value of the present invention is higher in patients who are PD-L1 positive, and in patients with squamous NSCLC. Therefore, in one embodiment, the biomarker of the present invention is used for predicting response of patients who are PD-L1 positive, more specifically patients with NSCLC who are PD-L1 positive, to a PD-1 axis inhibitor such as an anti-PD-L1 antibody atezolizumab. In another embodiment, the biomarker of the present invention is used for predicting response of patients with squamous NSCLC to a PD-1 axis inhibitor such as an anti-PD-L1 antibody atezolizumab.

Exemplary PD-1 Axis Inhibitors for Use in the Present Invention By way of example, a PD-1 axis inhibitor includes a PD-1 binding antagonist and a PD-L1 binding antagonist. Alternative names for "PD-1" include CD279 and SLEB2. Alternative names for "PD-L1" include B7-H1, B7-4, CD274, and B7-H. In some embodiments, PD-1 and PD-L1 are human PD-1 and PD-L1.

In some embodiments, the PD-1 binding antagonist is a molecule that inhibits the binding of PD-1 to its ligand binding partners. In a specific aspect the PD-1 ligand binding partners are PD-L1 and/or PDL2. In another embodiment, a PDL1 binding antagonist is a molecule that inhibits the binding of PD-L1 to its binding partners. In a specific aspect, PD-L1 binding partners are PD-1 and/or B7-1. The antagonist may be an antibody, an antigen binding fragment thereof, an immunoadhesin, a fusion protein, or oligopeptide.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab and pembrolizumab. In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. AMP-224, also known as B7-DCIg, is a PD-L2-Fc fusion soluble receptor described in WO2010/027827 and WO2011/066342.

In some embodiments, the PD-L1 binding antagonist is anti-PD-L1 antibody. In some embodiments, the anti-PDL1 binding antagonist is selected from the group consisting of YW243.55.570, MPDL3280A, MDX-1105, and MEDI4736. MDX-1105, also known as BMS-936559, is an anti-PDL1 antibody described in WO2007/005874. Antibody YW243.55.570 is an anti-PDL1 described in WO 2010/077634 A1. MEDI4736 is an anti-PDL1 antibody described in WO2011/066389 and US2013/034559.

Examples of anti-PD-L1 antibodies useful for the methods of this invention, and methods for making thereof are described in PCT patent application WO 2010/077634 A1 and U.S. Pat. No. 8,217,149, each incorporated herein by reference as if set forth in their entirety.

In some embodiments, the anti-PD-L1 antibody is atezolizumab (CAS Registry Number: 1422185-06-5). Atezolizumab (Genentech), also known as MPDL3280A, is an anti-PD-L1 antibody.

Atezolizumab comprises:

(a) an HVR-H1, HVR-H2, and HVR-H3 sequence of GFTFSDSWIH (SEQ ID NO:1), AWISPYGGSTYY-ADSVKG (SEQ ID NO:2) and RHWPGGFDY (SEQ ID NO:3), respectively, and (b) an HVR-L1, HVR-L2, and HVR-L3 sequence of RASQDVSTAVA (SEQ ID NO:4), SASFLYS (SEQ ID NO:5) and QQYLYHPAT (SEQ ID NO:6), respectively.

Atezolizumab comprises a heavy chain and a light chain sequence, wherein:

```
(a) the heavy chain variable region sequence
comprises the amino acid sequence:
                                        (SEQ ID NO: 7)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSS,
and (b) the light chain variable region sequence
comprises the amino acid sequence:
                                        (SEQ ID NO: 8)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.
```

Atezolizumab comprises a heavy chain and a light chain sequence, wherein:

```
(a) the heavy chain comprises the amino acid
sequence:
                                        (SEQ ID NO: 9)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYAST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPG,
and (b) the light chain comprises the amino acid
sequence:
                                        (SEQ ID NO: 10)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.
```

In some embodiments, the PD-1 axis binding antagonist is an anti-PD-L1 antibody. In some embodiments, the anti-PD-L1 antibody is capable of inhibiting binding between PD-L1 and PD-1 and/or between PD-L1 and B7-1. In some embodiments, the anti-PD-L1 antibody is a monoclonal antibody. In some embodiments, the anti-PD-L1 antibody is an antibody fragment selected from the group consisting of Fab, Fab'-SH, Fv, scFv, and (Fab')2 fragments. In some embodiments, the anti-PDL1 antibody is a humanized antibody. In some embodiments, the anti-PDL1 antibody is a human antibody.

The antibody or antigen binding fragment thereof, may be made using methods known in the art, for example, by a process comprising culturing a host cell containing nucleic acid encoding any of the previously described anti-PD-L1, anti-PD-1, or anti-PD-L2 antibodies or antigen-binding fragment in a form suitable for expression, under conditions suitable to produce such antibody or fragment, and recovering the antibody or fragment.

In any of the embodiments herein, the isolated anti-PDL1 antibody can bind to a human PDL1, for example a human PDL1 as shown in UniProtKB/Swiss-Prot Accession No.Q9NZQ7.1, or a variant thereof.

In a still further embodiment, the invention provides for a composition comprising an anti-PD-L1, an anti-PD-1, or an anti-PD-L2 antibody or antigen binding fragment thereof as provided herein and at least one pharmaceutically acceptable carrier. In some embodiments, the anti-PD-L1, anti-PD-1, or anti-PD-L2 antibody or antigen binding fragment thereof administered to the individual is a composition comprising one or more pharmaceutically acceptable carrier.

In some embodiments, the anti-PD-L1 antibody described herein is in a formulation comprising the antibody at an amount of about 60 mg/mL, histidine acetate in a concentration of about 20 mM, sucrose in a concentration of about 120 mM, and polysorbate (e.g., polysorbate 20) in a concentration of 0.04% (w/v), and the formulation has a pH of about 5.8. In some embodiments, the anti-PD-L1 antibody described herein is in a formulation comprising the antibody in an amount of about 125 mg/mL, histidine acetate in a concentration of about 20 mM, sucrose is in a concentration of about 240 mM, and polysorbate (e.g., polysorbate 20) in a concentration of 0.02% (w/v), and the formulation has a pH of about 5.5.

Assays for Use in the Present Invention

In some embodiments, the biomarker is detected in the sample using a method selected from the group consisting of FACS, Western blot, ELISA, immunoprecipitation, immunohistochemistry, immunofluorescence, radioimmunoassay, immunodetection methods, mass spectrometery, qPCR, RT-qPCR, multiplex qPCR or RT-qPCR, RNA-seq, microarray analysis, nanostring, SAGE, MassARRAY technique, and FISH, and combinations thereof. In some embodiments, the biomarker is detected in the sample by protein expression. In some embodiments, protein expression is determined by immunohistochemistry (IHC).

In some embodiments, the biomarker is detected in the sample by mRNA expression. In some embodiments, the mRNA expression is determined using qPCR, rtPCR, RNA-seq, multiplex qPCR or RT-qPCR, microarray analysis, nanostring, SAGE, MassARRAY technique, or FISH.

In some embodiments, the sample is a tumor tissue sample. In some embodiments, the tumor tissue sample comprises tumor cells, tumor infiltrating immune cells, stromal cells or any combinations thereof.

In some embodiments, the sample is obtained prior to treatment with a PD-L1 axis inhibitor. In some embodiments, the tissue sample is formalin fixed and paraffin embedded, archival, fresh or frozen.

Presence and/or expression level/amount of various biomarkers in a sample can be analyzed by a number of methodologies, many of which are known in the art and understood by the skilled artisan, including, but not limited to, immunohistochemistry ("IHC"), Western blot analysis, immunoprecipitation, molecular binding assays, ELISA, ELIFA, fluorescence activated cell sorting ("FACS"), MassARRAY, proteomics, quantitative blood based assays (as for example Serum ELISA), biochemical enzymatic activity assays, in situ hybridization, Southern analysis, Northern analysis, whole genome sequencing, polymerase chain reaction ("PCR") including quantitative real time PCR ("qRT-PCR") and other amplification type detection methods, such as, for example, branched DNA, SISBA, TMA and the like), RNA-Seq, FISH, microarray analysis, gene expression profiling, and/or serial analysis of gene expression ("SAGE"), as well as any one of the wide variety of assays that can be performed by protein, gene, and/or tissue array analysis. Typical protocols for evaluating the status of genes and gene products are found, for example in Ausubel et al., eds., 1995, Current Protocols In Molecular Biology, Units 2 (Northern Blotting), 4 (Southern Blotting), 15 (Immunoblotting) and 18 (PCR Analysis). Multiplexed immunoassays such as those available from Rules Based Medicine or Meso Scale Discovery ("MSD") may also be used.

In one embodiment, the sample is a clinical sample. In another embodiment, the sample is used in a diagnostic assay. In some embodiments, the sample is obtained from a primary or metastatic tumor. Tissue biopsy is often used to obtain a representative piece of tumor tissue.

In certain embodiments, a reference sample, reference tissue, control sample, or control tissue is a single sample or combined multiple samples from the same subject or individual that are obtained at one or more different time points than when the test sample is obtained. In certain embodiments, a reference sample, reference tissue, control sample, or control tissue is a combined multiple samples from one or more healthy individuals who are not the subject or individual. In certain embodiments, a reference sample, reference tissue, control sample, or control tissue is a combined multiple samples from one or more individuals with a disease or disorder (e.g., cancer) who are not the subject or individual.

In some embodiments, the sample is a tumor tissue sample (e.g., biopsy tissue). In some embodiments, the tissue sample is lung tissue. In some embodiments, the tissue sample is renal tissue. In some embodiments, the tissue sample is skin tissue. In some embodiments, the tissue sample is pancreatic tissue. In some embodiments, the tissue sample is gastric tissue. In some embodiments, the tissue sample is bladder tissue. In some embodiments, the tissue sample is esophageal tissue. In some embodiments, the tissue sample is mesothelial tissue. In some embodiments, the tissue sample is breast tissue. In some embodiments, the tissue sample is thyroid tissue. In some embodiments, the tissue sample is colorectal tissue. In some embodiments, the tissue sample is head and neck tissue. In some embodiments, the tissue sample is osteosarcoma tissue. In some embodiments, the tissue sample is prostate tissue. In some embodiments, the tissue sample is ovarian tissue, HCC (liver), blood cells, lymph nodes, bone/bone marrow.

Therapeutic Methods

Provided are methods for treating cancer in an individual, the method comprising: determining the abundance of DCs in a tumor tissue sample from the individual, and administering an effective amount of a PD-1 axis inhibitor to the individual.

In some embodiments, an increased expression of biomarkers related to development of DCs indicates that the individual is more likely to have increased clinical benefit when the individual is treated with the PD-L1 axis inhibitor. In some embodiments, the increased clinical benefit comprises a relative increase in one or more of the following: overall survival (OS), progression free survival (PFS), complete response (CR), partial response (PR) and combinations thereof.

PD-1 axis inhibitor described herein can be used either alone or in combination with other agents in a therapy. For instance, a PD-1 axis inhibitor described herein may be co-administered with at least one additional therapeutic agent. In certain embodiments, an additional therapeutic agent is a chemotherapeutic agent.

Such combination therapies noted above encompass combined administration (where two or more therapeutic agents are included in the same or separate formulations), and separate administration, in which case, administration of the antagonist can occur prior to, simultaneously, and/or following, administration of the additional therapeutic agent and/or adjuvant. PD-1 axis inhibitor described herein can also be used in combination with radiation therapy.

A PD-1 axis inhibitor (e.g., an antibody, binding polypeptide, and/or small molecule) described herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various timepoints, bolus administration, and pulse infusion are contemplated herein.

PD-1 axis inhibitor (e.g., an antibody, binding polypeptide, and/or small molecule) described herein may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The PD-1 axis inhibitor need not be, but is optionally formulated with one or more agents currently used to prevent or treat the disorder in question. The effective amount of such other agents depends on the amount of the PD-1 axis inhibitor present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a PD-1 axis inhibitor described herein (when used alone or in combination with one or more other additional therapeutic agents) will depend on the type of disease to be treated, the severity and course of the disease, whether the PD-1 axis inhibitor is administered for preventive or therapeutic purposes, previous therapy, the patient's clinical history and response to the PD-1 axis inhibitor, and the discretion of the attending physician. The PD-1 axis inhibitor is suitably administered to the patient at one time or over a series of treatments. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. Such doses may be administered intermittently, e.g., every week or every three weeks (e.g., such that the patient receives from about two to about twenty, or e.g., about six doses of the PD-1 axis inhibitor). An initial higher loading dose, followed by one or more lower doses may be administered. An exemplary dosing regimen comprises administering. However, other dosage regimens may be useful. The progress of this therapy is easily monitored by conventional techniques and assays.

In some embodiments, the PD-1 axis inhibitor (e.g., anti-PD-L1 antibody) is administered at a dosage of about 0.3-30 mg/kg. In some embodiments, the PD-L1 axis binding antagonist (e.g., anti-PD-L1 antibody) is administered at a dosage of about any of 0.3 mg/kg, 0.5 mg/kg, 1 mg/kg, 2 mg/kg, 4 mg/kg, 8 mg/kg, 15 mg/kg, 20 mg/kg, or 30 mg/kg. In some embodiments, the PD-1 axis inhibitor (e.g., anti-PD-L1 antibody) is administered at a dosage of about any of 2 mg/kg, 4 mg/kg, 8 mg/kg, 15 mg/kg, or 30 mg/kg in 21-day cycles. It is understood that any of the above formulations or therapeutic methods may be carried out using an immunoconjugate in place of or in addition to the PD-1 axis inhibitor.

Pharmaceutical formulations of a PD-1 axis inhibitor as described herein are prepared by mixing such antibody having the desired degree of purity with one or more optional pharmaceutically acceptable carriers (Remington's Pharmaceutical Sciences 16th edition, Osol, A. Ed. (1980)), in the form of lyophilized formulations or aqueous solutions. In some embodiments, the PD-1 axis inhibitor is a binding small molecule, an antibody, binding polypeptide, and/or polynucleotide. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one embodiment, a sHASEGP is combined with one or more additional glycosaminoglycanases such as chondroitinases.

Exemplary lyophilized formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the PD-L1 axis binding antagonist, which matrices are in the form of shaped articles, e.g., films, or microcapsules.

The formulations to be used for in vivo administration are generally sterile. Sterility may be readily accomplished, e.g., by filtration through sterile filtration membranes.

Diagnostic Kits, Assays and Articles of Manufacture

Provided herein are diagnostic kit comprising one or more reagent for determining the presence of a biomarker in a sample from an individual with a disease or disorder.

Provided herein are also assay for identifying an individual with a disease or disorder to receive a PD-L1 axis inhibitor, the method comprising: determining the abundance of DCs in a tumor tissue sample from the individual, and recommending a PD-1 axis inhibitor based on the abundance of DCs.

Provided herein are also articles of manufacture comprising, packaged together, a PD-L1 axis inhibitor (e.g., anti-PD-L1 antibodies) in a pharmaceutically acceptable carrier and a package insert indicating that the PD-L1 axis inhibitor (e.g., anti-PD-L1 antibodies) is for treating a patient with a disease or disorder based on abundance of DCs or expression levels biomarkers related to development of DCs. Treatment methods include any of the treatment methods disclosed herein. Further provided are a method for manufacturing an article of manufacture comprising combining in a package a pharmaceutical composition comprising a PD-1 axis inhibitor (e.g., anti-PD-L1 antibodies) and a package insert indicating that the pharmaceutical composition is for treating a patient with a disease or disorder based on abundance of DCs or expression levels of biomarkers related to development of DCs.

The article of manufacture comprises a container and a label or package insert on or associated with the container. Suitable containers include, for example, bottles, vials, syringes, etc. The containers may be formed from a variety of materials such as glass or plastic. The container holds or contains a composition comprising the cancer medicament as the active agent and may have a sterile access port (for example the container may be an intravenous solution bag or a vial having a stopper pierceable by a hypodermic injection needle).

The article of manufacture may further comprise a second container comprising a pharmaceutically-acceptable diluent buffer, such as bacteriostatic water for injection (BWFI), phosphate-buffered saline, Ringer's solution and dextrose solution. The article of manufacture may further include other materials desirable from a commercial and user standpoint, including other buffers, diluents, filters, needles, and syringes.

The article of manufacture of the present invention also includes information, for example in the form of a package insert, indicating that the composition is used for treating cancer based on expression level of the biomarker(s) herein. The insert or label may take any form, such as paper or on electronic media such as a magnetically recorded medium (e.g., floppy disk) or a CD-ROM. The label or insert may also include other information concerning the pharmaceutical compositions and dosage forms in the kit or article of manufacture.

The present invention is further described by reference to the following non-limited figures and examples.

EXAMPLES

Example 1: PD-1 and PD-L1 are Negatively Correlated on Human DCs

To address the potential regulation of PD-1 and its ligands on human DCs, monocyte-derived DCs were generated using the classical method. Briefly, Peripheral Blood Mononuclear Cells (PBMCs) were isolated from buffy-coats (Blutspende, Schlieren) from healthy human donors, using Ficoll-Paque™ Plus (GE Healthcare, #17-1440-03) density gradient. Rings of PBMCs were collected and washed with PBS two times by centrifugation (5' at 763 g; 5' at 600 g). A lysis was conducted using 10 mL of BD Pharm Lyse™ (BD Biosciences, #555899) diluted at 1× with sterile water and incubated 1,5 minute at room temperature. Two washes with Phosphate-buffered saline 1× (PBS; Gibco® by live technologies™, #20012-019) were conducted by centrifugation (8' at 135 g). Cells number and quality were evaluated using Cell counter (Beckman Coulter®). Separate unrelated donors were used for each independent experiment. Monocytes were isolated from fresh PBMCs by negative selection using Human monocyte enrichment kit (StemCell, #19059) in MACs buffer (1450 mL Automacs™ Rinsing solution, Miltenyi #130-091-222; and 75 mL MACS BSA stock Solution, Miltenyi #130-091-376) according to the manufacturer's instructions. Purity was checked using Cell counter (Beckman Coulter®), monocytes were routinely >95% pure.

Monocytes were seed in 6-well plates with $1,5 \times 10^6$ cells/well in 2 mL of Medium (RPMI 1640 (1×) Glutamax; 10% Heat-Inactivated Fetal Bovine Serum (FBS) and 1% Penicillin-Streptomycin, all from Gibco®) at 37° C. and incubated 2 hours (37° C., atmosphere 5% $CO_2$). After 2 hours of incubation one more selection was processed by plastic adherence; the medium was removed and 2 mL/well of fresh Medium supplemented with 10 µg/mL of recombinant human Interleukine-4 and Granulocyte Macrophage Colony-Stimulating Factor (IL-4 and GM-CSF; R&D Systems, #204-IL; #215-GM) were added. Plates were incubated at 37° C. in an atmosphere with 5% $CO_2$. On day 2, 200 µL/well of Medium at 37° C. supplemented with 100 µg/mL (10×) of recombinant human IL-4 and GM-CSF were added. On day 4, 1 mL of Medium at 37° C. supplemented with 30 µg/mL (3×) of recombinant human IL-4 and GM-CSF were added. After five days of culture, in vitro monocyte-derived DCs are fully differentiated. The cells were then stained with anti-PD-1-PE-Cy7 and anti-PD-L1-APC Abs (BioLegend®; #329917, #329707), and measured by flow cytometry (BD).

Figure 1B:
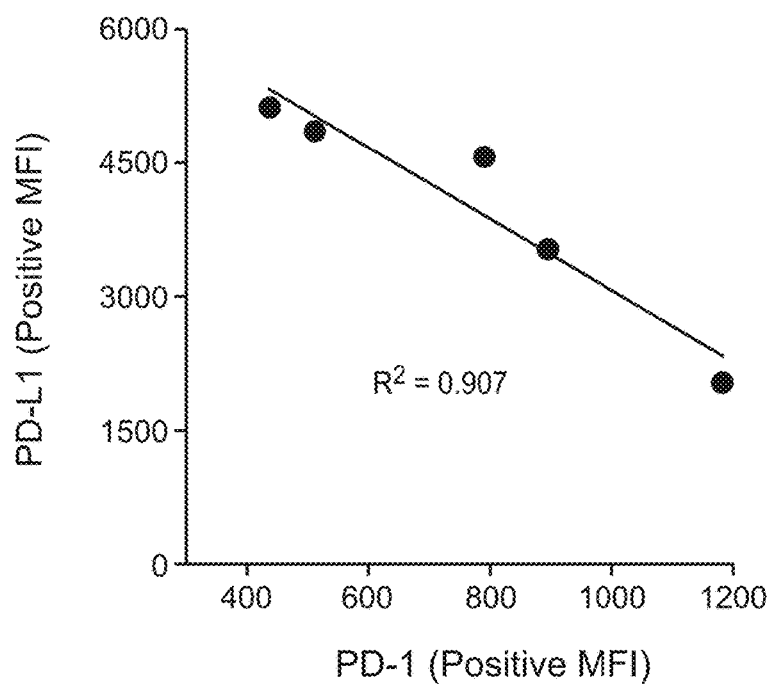
Figure 2A:
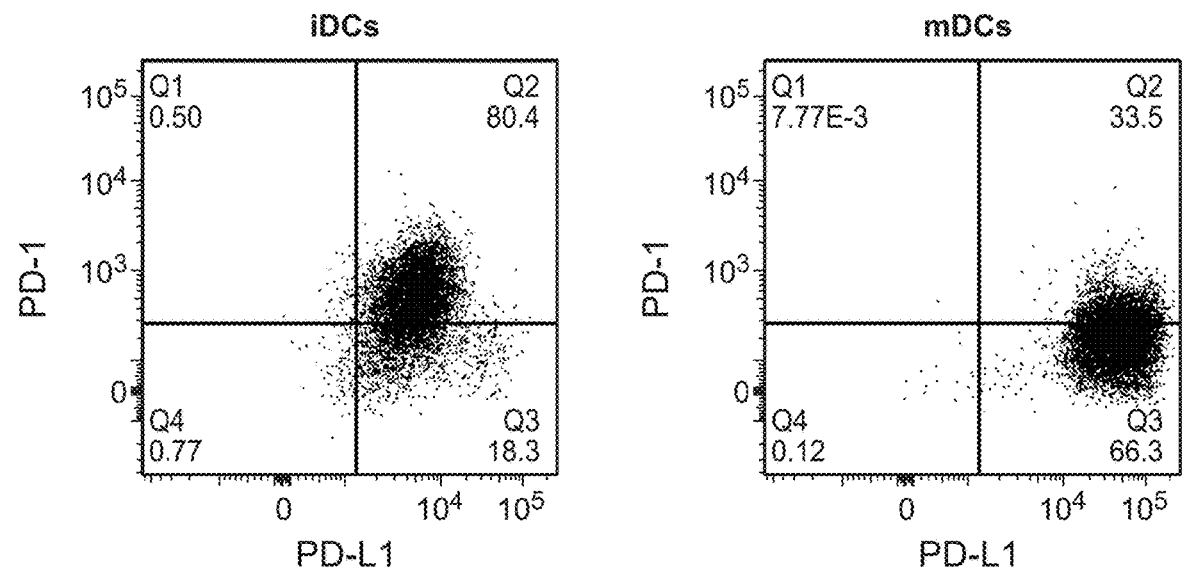
FIGS. 2A-2B show that upon maturation of DCs, PD-1 is downregulated while PD-L1 is upregulated (FIGS. 2A and 2B).
Figure 2B:
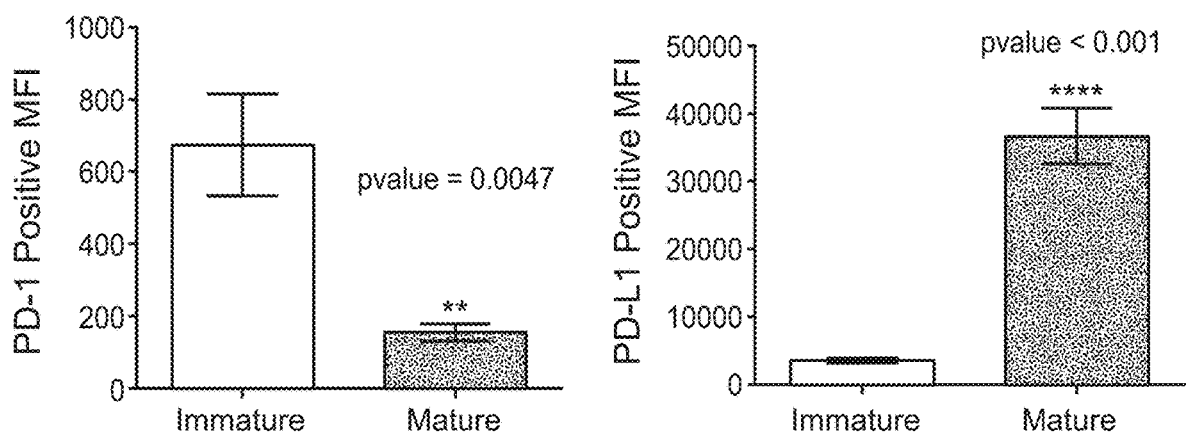
Figure 3A:
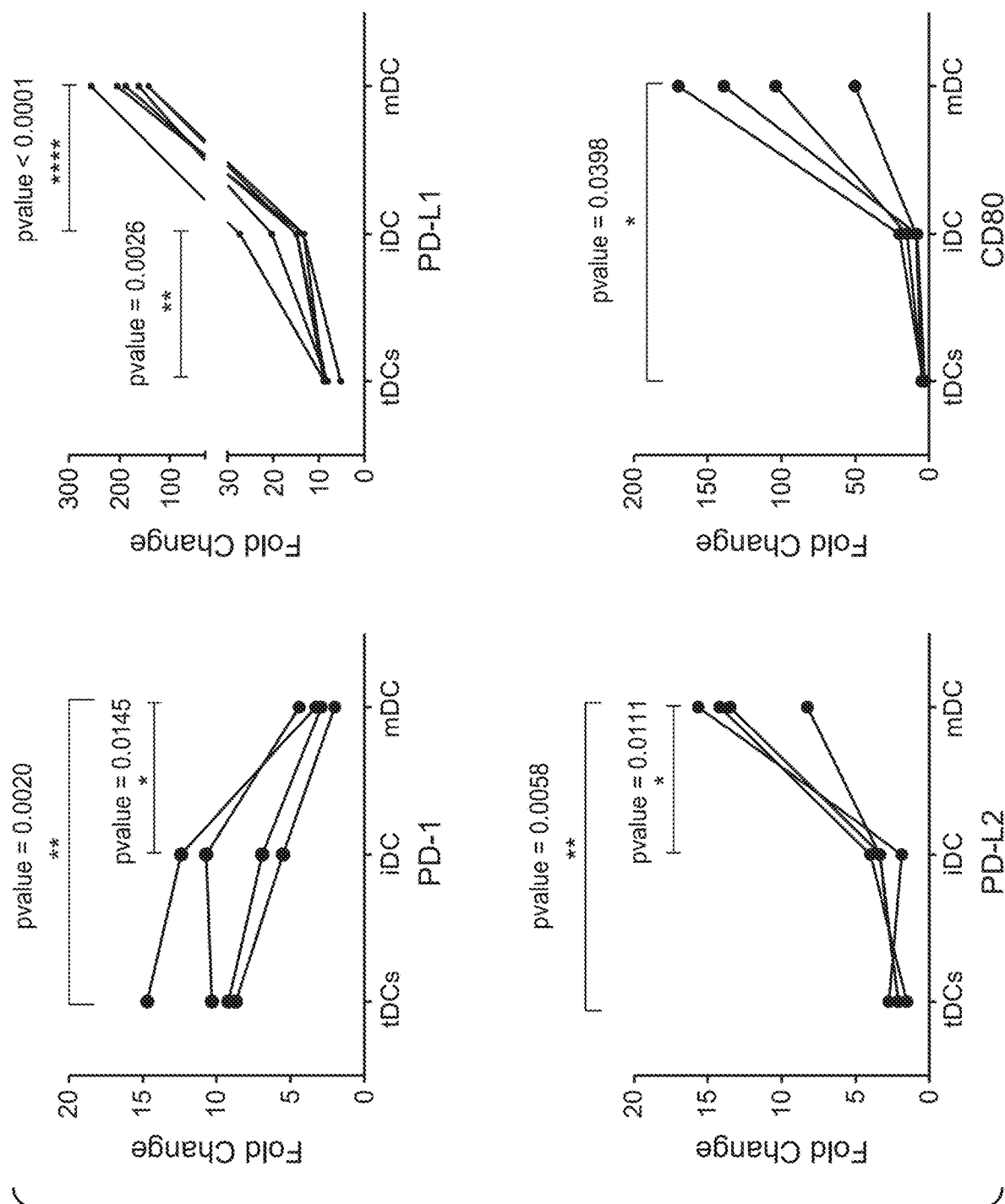
FIGS. 3A-3B show the results of the immunostaining of immature DCs (iDCs), mature DCs (mDCs) and tolerogenic DCs (tDCs) (FIG. 3A) and the flow cytometry measurement of T cell proliferation in T cells co-cultured with different DCs (FIG. 3B). These figures show that the expression profile of PD-1 is negatively correlated with T cell stimulatory capacity.

We observed that human DCs express both PD-1 and PD-L1 (FIG. 1A), the expression profile of PD-1 and PD-L1 is negatively correlated ($R^2=0.907$) (FIG. 1B). Upon maturation of DCs by LPS of lipopolysaccharide (LPS, 10 ng/mL Sigma-Aldrich, #L4516), PD-1 is downregulated, while PD-L1 is upregulated (FIGS. 2A-2B), which prompted us to hypothesize that PD-1 is a functionally negative regulator on DCs. To test this, we generated tolerogenic DCs (tDCs, a subset that are impaired in stimulating T cell proliferation) following a protocol (van Kooten et al., 2011, Methods Mol Biol, 677: 149-59) by adding Dexamethasone (Sigma, #D2915) at a final concentration of 0.39 µg/mL in addition of IL-4 and GM-CSF. For head-to-head comparison, immature DCs (iDCs), mature DCs (mDCs) and tDCs were generated in parallel from monocytes of the same donor. The cells were stained for the expression of PD-1, PD-L1, PD-L2 and CD80. tDCs showed the highest level of PD-1 while lowest level of PD-L1, as compared to other DCs (FIG. 3A). The expression PD-L2 and CD80 have the same pattern as PD-L1 expression (FIG. 3A).

Figure 3B:
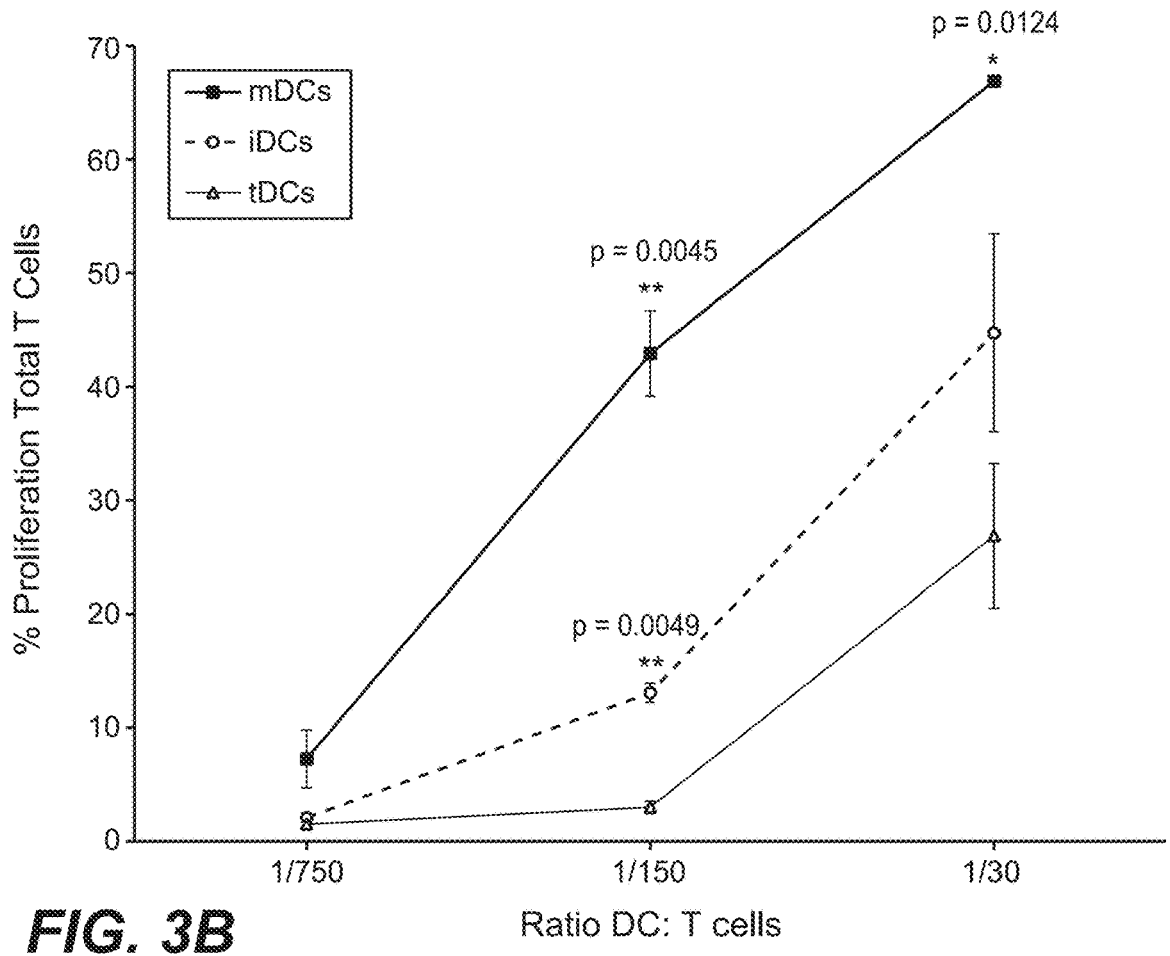

To confirm a correlation of PD-1 expression with their functionality of T cell stimulation, a mixed lymphocytes reaction was performed by co-culture with allogeneic total T cells isolated from frozen PBMCs (from a different donor than in vitro generated monocytes-derived DCs). The isolation of T cells was done by negative selection using Pan T cell Isolation kit human (Miltenyi Biotec, #130-096-535) following manufacturer's instructions. Total T cells were routinely >95% pure. T cells were resuspended at $1 \times 10^7$ cells/mL in PBS. 1 mL of Carboxyfluorescein succinimidyl ester (CFSE Proliferation Dye, eBioscience, #65-0850-84) at 5 nM in PBS was added per $10^7$ T cells protected from light and incubated 7 minutes in a thermal bath at 37° C. 10 mL of cold RPMI were added and after a wash by centrifugation (6' at 475 g), cell number of CFSE-stained T cell was determined using Automated cell counter Countess™ after a Trypan blue coloration dilution 1 to 2. 100 μL/well of medium at 37° C. containing 150k T cells were seed in a 96-well plate and incubated at 37° C. in an atmosphere with 5% $CO_2$. 100 μL/well of DCs (or activated mDCs) were added to CFSE stained T cells at the following T cell: DCs ratios; 1:30, 1:150 and 1:750. For each condition, duplicate or triplicate wells were prepared. The co-culture was incubated at 37° C. in an atmosphere with 5% $CO_2$. After 5 days, the plate was centrifuged (7' at 600 g), supernatants were stored at minus 80° C. were stained for T cells proliferation analysis (CFSE dilution) by Flow Cytometry. Data presented in FIG. 3B indicate that PD-1$^-$ mDCs are able to stimulate T cell proliferation, whereas PD-1$^+$ tDCs failed to activate T cells. Thus, the expression profile of PD-1 is negatively correlated with their T cell stimulatory capacity.

Figure 4A:
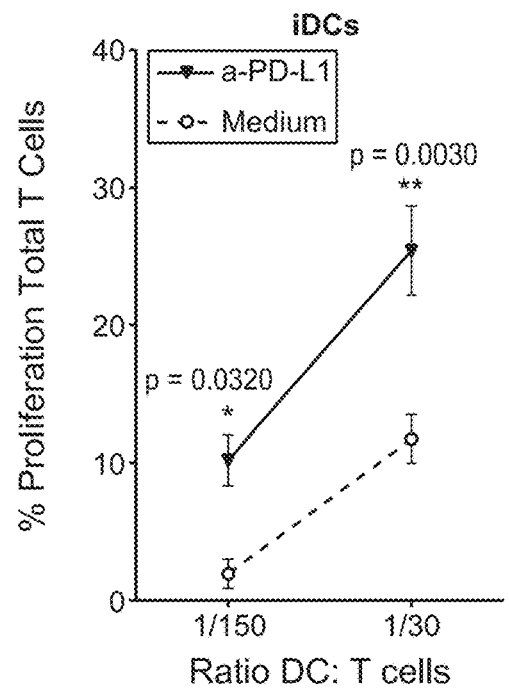
FIGS. 4A-4B show that DCs pre-incubated with an anti-PD-L1 Ab acquired enhanced T cell stimulatory capacity (FIG. 4A), accompanied with increased IFN-γ production (FIG. 4B).
Figure 4B:
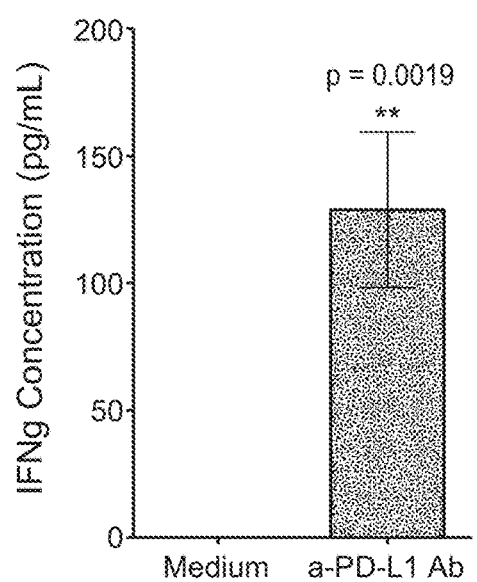

We next studied the direct effect of PD-1 inhibition on DCs. iDCs that were treated with an anti-PD-1 mAb or anti-PD-L1 mAb led to the upregulation of co-stimulatory molecules such as CD80, CD86, CD83 and CD40. We then tested whether a blocking Ab of PD-L1 would activate directly DCs to acquire enhanced T cell stimulatory capacity. iDCs were pre-activated with or without blocking PD-L1 Ab (10 μg/mL, generated in-house at Roche, #7569), or in some cases, with 10 μg/mL of the isotype control antibody (generated in-house at Roche; #4852) overnight for 18 hours, and extensively washed prior to co-culture with allogenic T cells in a mixed lymphocyte reaction for additional 5 days. Supernatant were harvested for measurement of IFN-γ by ELISA (R&D Systems, #DY285), and the T cells were harvested for measurement of proliferation by flow cytometry. We observed that DCs pre-incubated with PD-L1 Ab acquired enhanced T cell stimulatory capacity (FIG. 4A), accompanied with increased IFN-γ production by activated T cells (FIG. 4B). This shows that PD-L1/PD-1 blockade-based cancer therapy can directly target DCs to potentially promote T cell priming and/or re-stimulation.

PD-L1 binds to both CD80 and PD-1. However the PD-L1/B7.1 interaction has a three-fold higher affinity than the CD80/CD28 interaction. To understand the complex interactions among PD-L1/PD-1 and PD-L1/CD80, we used confocal imaging to assess their localization on the surface of DCs. PD-1+ iDCs expressed a low level of CD80, which doesn't co-localize with PD-1. In contrast, PD-1- mDCs acquired higher expression of PD-L1 and CD80. Interestingly, the CD80 now co-localized with PD-L1, suggesting that the expression of PD-L1 in mDCs was binding to and sequestering CD80. Thus we questioned to what extent these molecules are involved in the formation of the DC-T-cell immunological synapse. CD28 and PD-1 were both polarized to the immunological synapse at the intersection of DCs and T cells. This suggests that PD-1 and CD28 are participating within the immunological synapse during TCR signaling. This is consistent with the recent finding that PD-1 signaling leads to dephosphorylation of CD28 on T cells. However, both PD-L1 and CD80 on mDCs had no or little interaction with PD-1 and/or CD28 in the synapse. This is again likely due to the higher binding affinity of the PD-L1/CD80 interaction versus the CD80/CD28 interaction.

The lack of strong interaction between mDC-derived CD80 and T cell-associated CD28 prompted us to further question whether disrupting PD-L1/CD80 interaction by a PD-L1 blocking Ab can promote the release of CD80, making it available to CD28, leading to co-stimulation of T cells. Indeed, pre-incubating mDCs with an anti-PD-L1 mAb enabled strong interaction of CD80 and CD28 at the contact of DCs and T cells. In contrast, an anti-PD-1 mAb, which does not interfere with the binding of PD-L1 to CD80, showed no influence on CD80 polarization. These data strongly support that an anti-PD-L1 mAb may have two distinct effects on the ability of DCs to activate T cells: 1.) blocking the PD-L1-mediated PD-1 signaling on PD-1+ iDCs to promote maturation; 2) dissociating of PD-L1 from B7.1 on mature DCs, freeing B7.1 to bind to CD28 for co-stimulation.

Figure 5A:
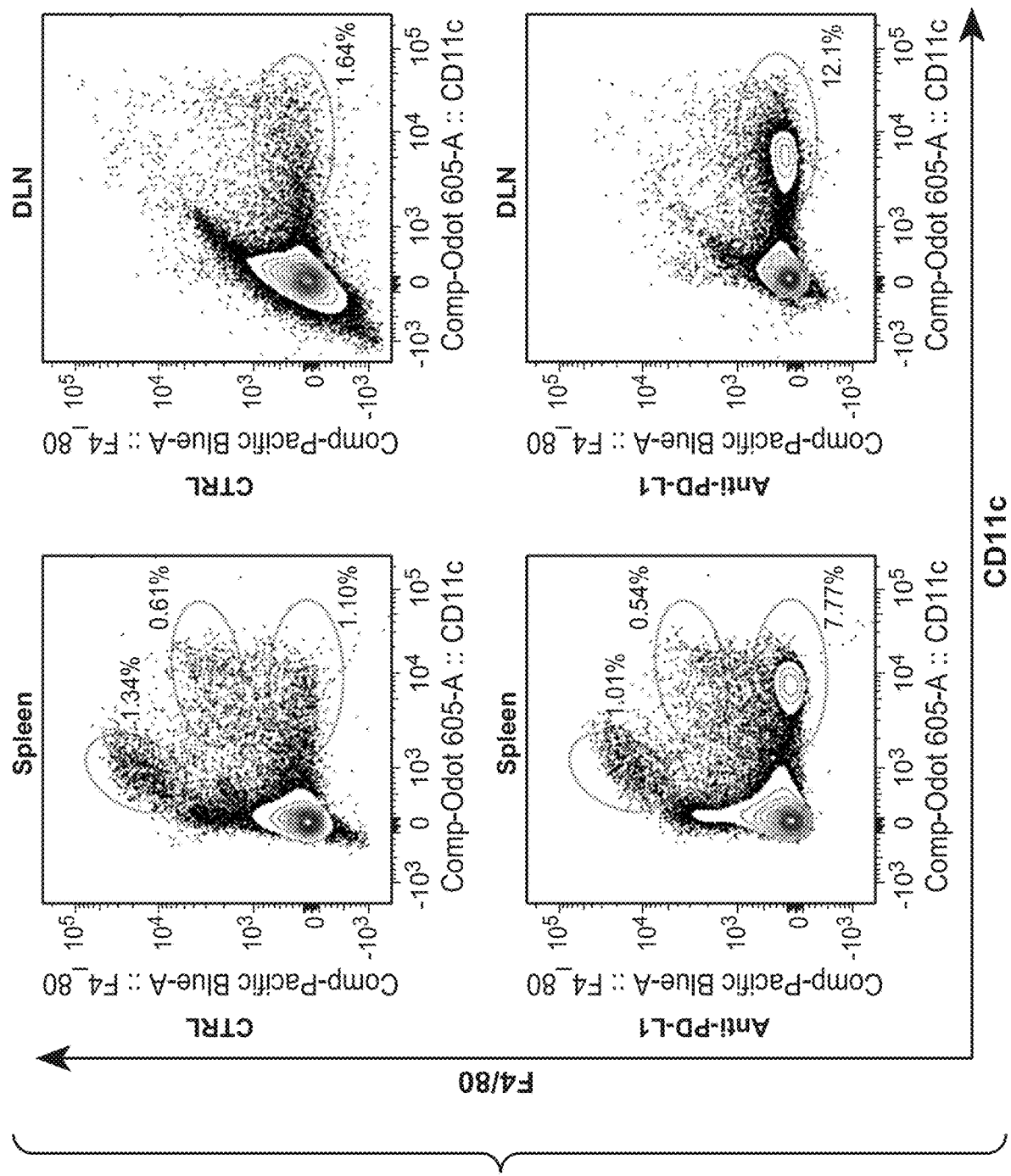
FIGS. 5A-5C shows tumor-bearing mice received PD-L1 Ab showed increased frequency of DCs in spleen and draining-lymph nodes (DLN) as compared to the vehicle group (FIGS. 5A-B), and the DCs (gated on CD11c+ cells) showed higher expression of CD86, a marker of activation/maturation (FIG. 5C).
Figure 5B:
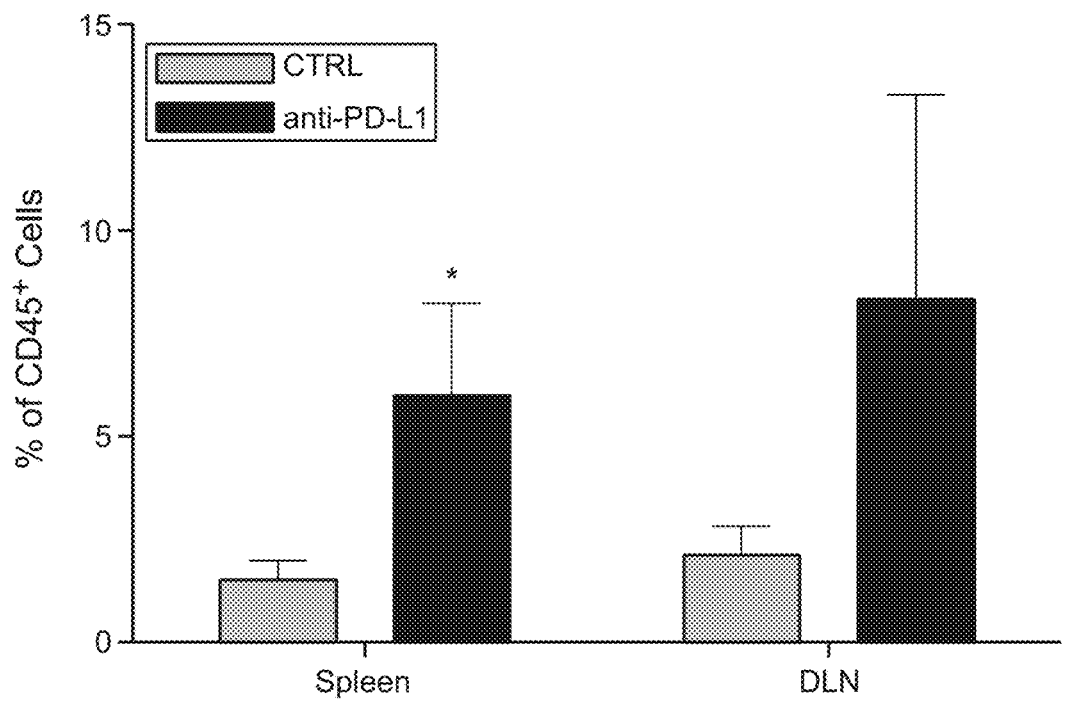
Figure 5C:
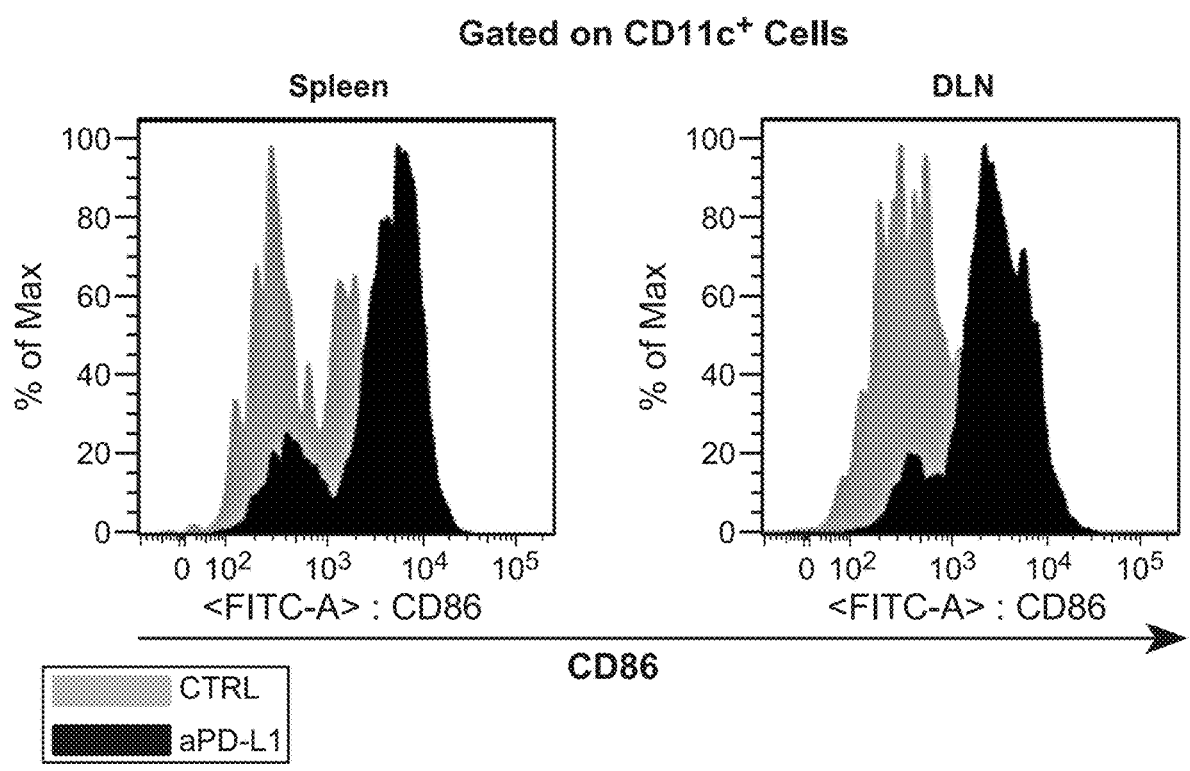

Example 2: Requirement of DCs in Tumor-Bearing Mice to Respond to PD-L1 Blockade To confirm the physiological relevance of above in vitro findings, we tested the anti-PD-L1 activities in in vivo animal models. We first set up an orthotopic tumor model of C57BL/6J female mice where PanC02-H7 (mouse pancreatic carcinoma cells originally obtained from University of Texas M. D. Anderson Cancer Center under a MTA) ($1 \times 10^5$ cells) were injected into the pancreas. Seven days later, an anti-PD-L1 Ab (10 mg/kg, murine IgG1, clone 6E11, Genentech) was administered intravenously (i.v.), and mice were harvested at 3 days after the treatment. We analyzed the CD11c+F4/80- DCs in the spleen and draining lymph nodes, and found that mice received anti-PD-L1 Ab showed increased frequency of DCs as compared to the vehicle group (FIGS. 5A-5B). Furthermore, DCs (gated on CD11c+ cells) showed higher expression of CD86 (FIG. 5C), a marker of activation/maturation. These data suggest that anti-PD-L1 Ab directly activates DCs in vivo.

Figure 6A:
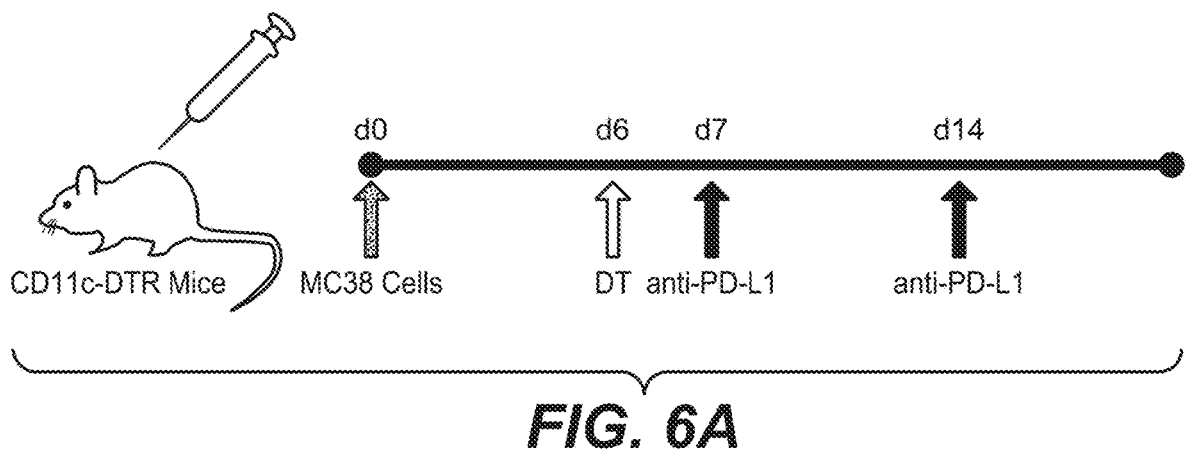
FIG. 6A shows the experimental design of an in vivo study of using CD11c-DTR mice where CD11c$^+$ DCs can be depleted by administration of diphtheria toxin (DT) prior to the treatment of an anti-PD-L1 antibody.
Figure 6B:
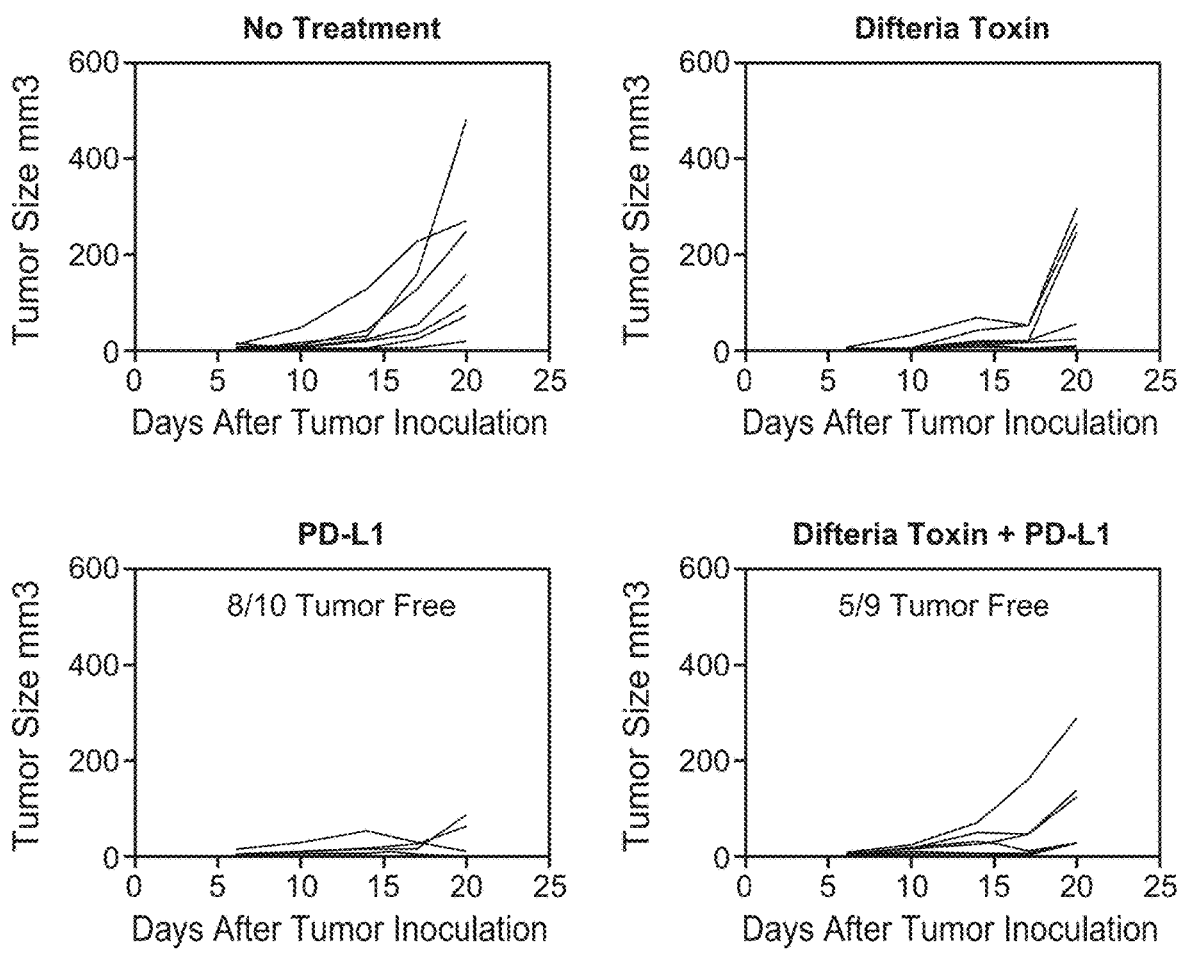
FIG. 6B shows that anti-PD-L1 antibody-mediated tumor growth inhibition is compromised in mice that DCs were depleted by DT.

To further study the contribution of DCs by PD-L1 blockade in mediating anti-tumor immunity, we obtained the CD11c-DTR mice from the Jackson laboratory (B6.FVB-Tg(Itgax-DTR/EGFP)57Lan/J, Cat. No. 004509). CD11c-DTR mice are BALB/c mice transgenic for a high affinity human diphtheria toxin (DT) receptor expressed under the cd11c promoter (Jung et al., 2002, Immunity, 17: 211-20), therefore DCs can be effectively depleted by administration of DT. Mice were injected subcutaneously (s.c.) on study day 0 with $0.2 \times 10^6$ of MC38 cells (colorectal cancer cell lines) obtained from ATCC) in RPMI medium. When tumor is palpable at day 6, mice were treated with 100 ng of DT (Sigma-Aldrich) or left untreated. At day 7, a anti-PD-L1 Ab (10 mg/kg, murine IgG1, clone 6E11, Genentech) was given to mice, followed by weekly injection (FIG. 6A). DT treatment alone did not impact the tumor growth in these mice (FIG. 6B). Anti-PD-L1 Ab treatment delayed tumor growth, and had eradicated tumors in 8/10 mice, whereas in mice depleted for DCs, anti-PD-L1 Ab efficacy was compromised significantly as only 5/9 mice were tumor-free in the end of the study (FIG. 6B). Our data support the concept that DCs are needed for PD-L1 Ab to achieve its maximum anti-tumor efficacy.

Example 3: DC Gene Transcripts Predict Clinical Benefit in Patients with Renal Cell Carcinoma Treated with Atezolizumab We hypothesized that patients with DC abundance may respond to PD-L1 blockade leading to beneficial effect in patients who received the treatment. We analyzed 56 patients with renal cell carcinoma who received Atezolizumab in a Phase I clinical trial (NCT01375842) (www.clinicaltrials.gov). This study was sponsored by Genentech Inc., a member of the Roche Group, which provided the study drug. The protocol and its amendments were approved by the relevant institutional review boards or ethics committees, and all participants provided written informed consent. This study was conducted in accordance with the Declaration of Helsinki and International Conference on Harmonization Guidelines for Good Clinical Practice. In total, 56 patients were analyzed. Based on the "Best Confirmed Overall Response by the Investigator" we observed 6 responders (CR=1; PR=5) and 47 non-responder (PD=21; SD=26) as well as 3 patients without known information (FIG. 7).

Figure 8A:
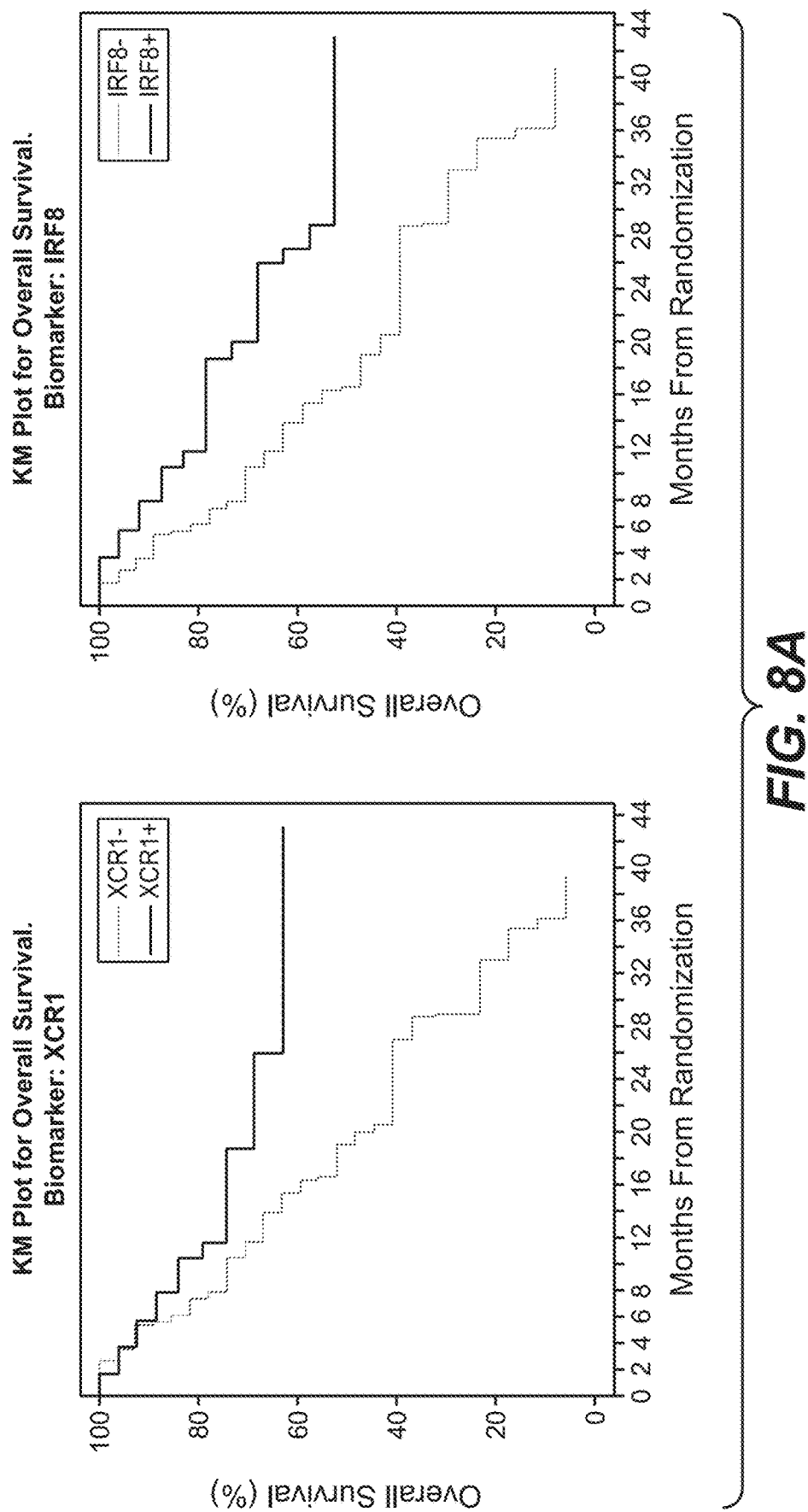
FIGS. 8A-8B show the Kaplan-Meier survival curves in patients with RCC. Expression of genes related to DC development correlates with the survival advantages by a PD-1 axis inhibitor atezolizumab.
Figure 8B:
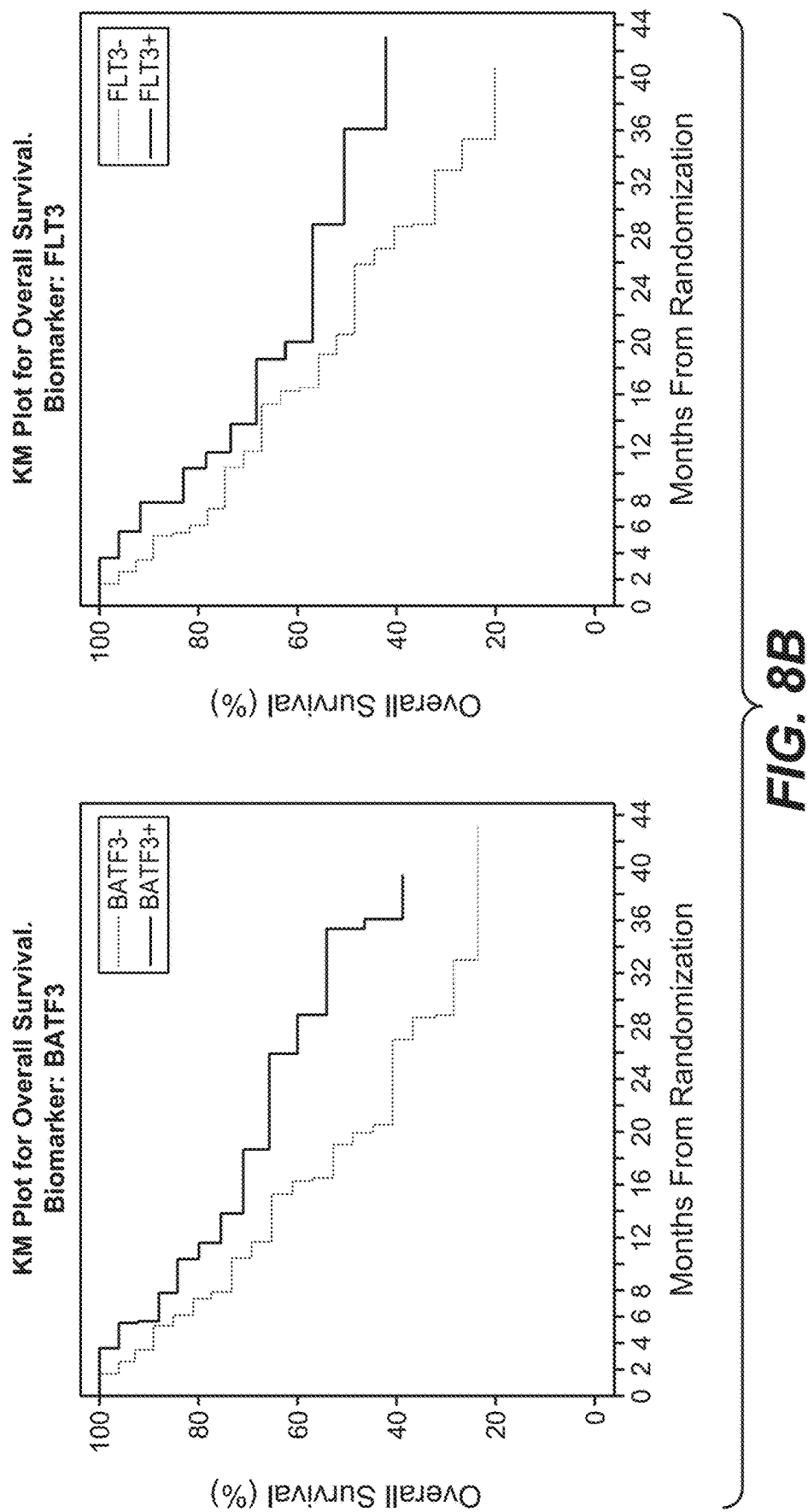

Tumor specimens at baseline were archived and taken for gene expression profiling performed by RNA Sequencing (RNA-Seq). Based on literature (Merad, ann rev immunol 2013), we selected a list of genes consisting of XCR1, IRF8, BATF3 and FLT3, which are associated with human dendritic cell development with cross-presenting specialization. The log 2 RPKM expression values of each selected gene across the whole cohort were divided at medium expression level for the higher expression ones (+) and lower/no expression ones (−). Using in-house R scripts the two defined subgroups were plotted against the Kaplan-Meier survival curves. FIGS. 8A-8B shows that every single gene expression pattern correlates with the survival advantages. The medium survival between patients with higher expression versus lower/no expression were separated for at least 15.6 months or longer (FIG. 9).

Figure 10:
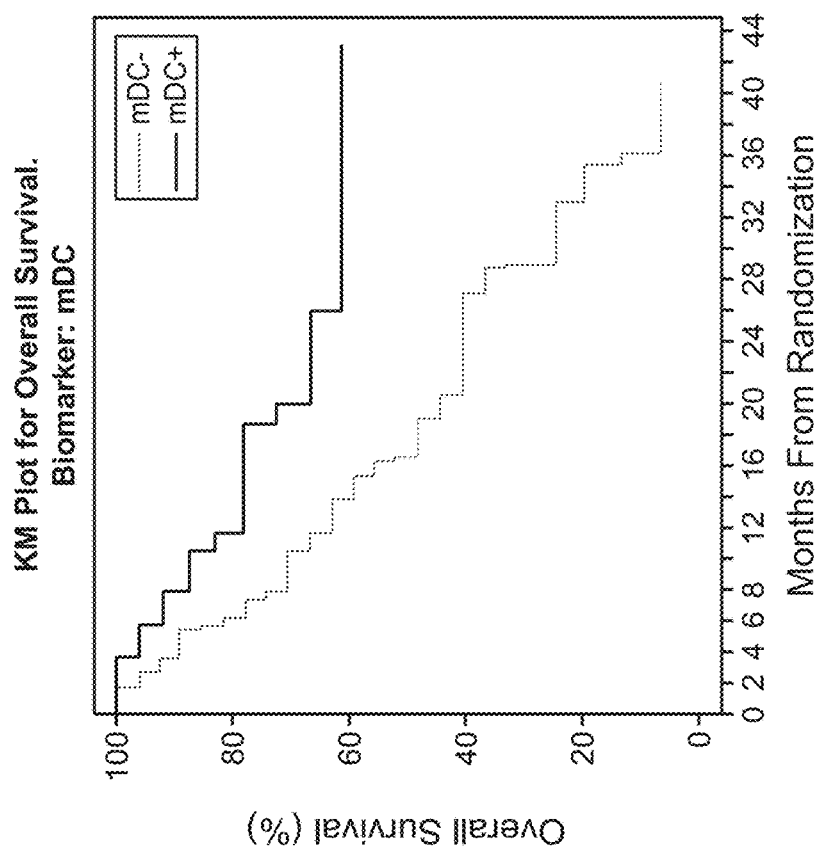
FIG. 10 shows the Kaplan-Meier survival curves based on the expression of a cumulative DC gene signature including genes: IRF8, FLT3, BATF3 and XCR1. A higher DC signature score correlates with clinical benefit to a PD-1 axis inhibitor atezolizumab in patients with RCC.

As several genes linked to human dendritic cell development were associated with the survival advantages, we investigated the impact of multiple genes involved in human DC development and function by defining a cumulative DC gene score (DC score) reflecting the cumulative expression of these marker genes. Each gene's expression is first standardized by a z-score:

$$z = (x-\mu)/\sigma,$$

where $\mu$ and $\sigma$ are estimated in the entire cohort or in the selected subgroups. After the standardization step, these standardized z-score values are averaged across genes within each patient. The RCC cohort was corrected for the sex of patient as well as the Stage at Initial Diagnosis. Based on such a analysis, we observed that patients with higher DC score showed superior survival advantage, without reaching medium survival, whereas the lower/no expression group had a medium survival of −18 months (HR=0.38, and p=0.03) (FIG. 10).

Example 4: DC Gene Transcripts Predict Clinical Benefit in Patients with NSCLC Treated with Atezolizumab Further to Example 3, we analyzed 193 patients with non-small cell lung cancer (NSCLC) previously treated, then received atezolizumab or docetaxel in a Phase II clinical trial POPLAR. This study is registered with ClinicalTrials.gov, number NCT01903993. POPLAR is a multicentre, randomised, open-label phase II trial, done at 61 academic medical centers and community oncology practices across 13 countries in Europe and North America. The study was done in full accordance with the guidelines for Good Clinical Practice and the Declaration of Helsinki. Protocol (and modification) approval was obtained from an independent ethics committee for each site (Fehrenbacher L, et. Al., Lancet 2016). Among those patients with squamous or non-squamous NSCLC, 96 received Docetaxel, and 92 received atezolizumab, and the rest of 5 left untreated (Table 1).

TABLE 1

Patient information in POPLAR study

| Treatment | Squamous | Non-squamous | Total |
|---|---|---|---|
| docetaxel | 36 | 60 | 96 |
| atezolizumab | 34 | 58 | 92 |
| not treated | 1 | 4 | 5 |

Tumor specimens at baseline were archived and taken for gene expression profiling performed by RNA Sequencing (RNA-Seq). Based on literature (Merad M. et al, Ann. Rev. Immunol. 2013), we selected a list of genes consisting of XCR1, IRF8, BATF3, and FLT3, which are associated with human dendritic cell phenotypes and development with cross-presenting specialization. Normalized read counts of each selected gene across the whole cohort were divided at medium expression level for the higher expression ones (+) and lower/no expression ones (−). Using in-house R scripts the two defined subgroups were plotted against the Kaplan-Meier survival curves. In addition, Cox-regression analysis was used to calculate the hazard ratio (HR) between the two patient groups divided based on positive and negative gene expression.

We also investigated the impact of multiple genes involved in human DC development and function (XCR1, BATF3, FLT3, and IRF8) by defining a cumulative DC gene score (DC score) reflecting the cumulative expression of these marker genes. Each gene's expression is first standardized by a z-score:

$$z = \frac{x-\mu}{\sigma},$$

where $\mu$ and $\sigma$ are estimated in the entire cohort or in the selected subgroups. After the standardization step, these standardized z-score values are averaged across genes within each patient. The cohort was corrected for the smoking status, ECOG and sex of patient. Then the score was plotted against the Kaplan-Meier survival curves.

Results

XCR1 gene expression pattern correlates with the survival advantages to atezolizumab. The medium overall survival (OS) between patients with higher expression versus lower/no expression were separated for ~7 months (mOS=8.6 versus 15.5 month), all with a statistically significant hazard ratio (HR) of 0.6 (p=0.077) by Cox-regression analysis. In contrast, there is no correlation of XCR1 expression to survival in patients received docetaxel.

Figure 11:
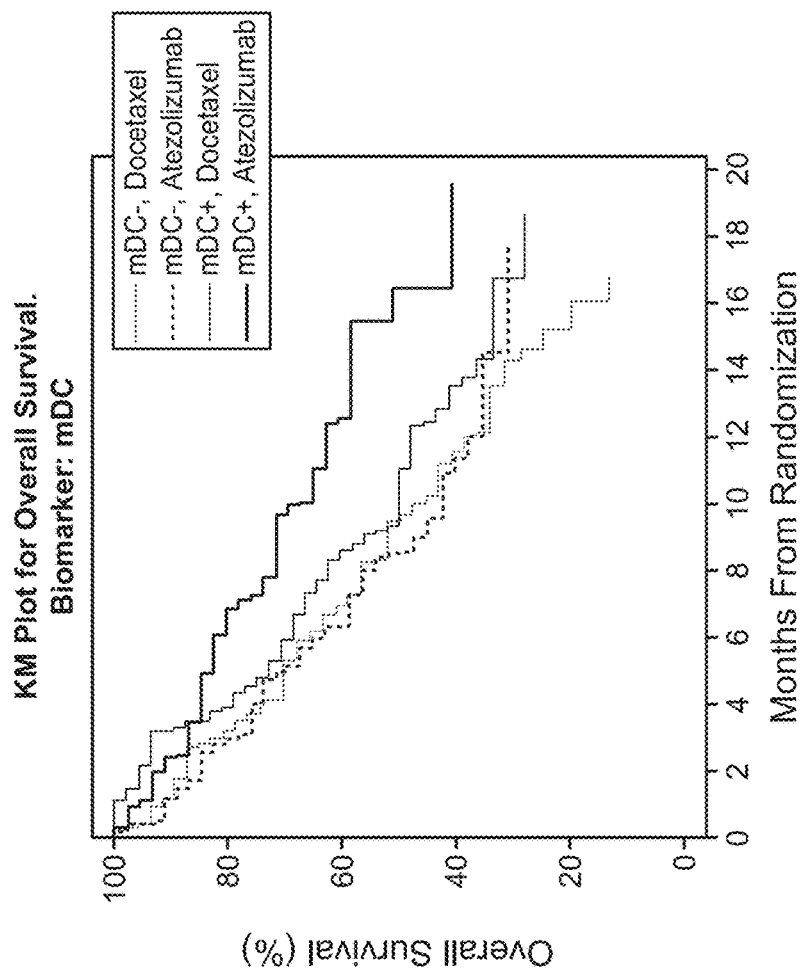
FIG. 11 shows that DC-related gene signature correlates with survival in patients with NSCLC treated with atezolizumab.
Figure 12:
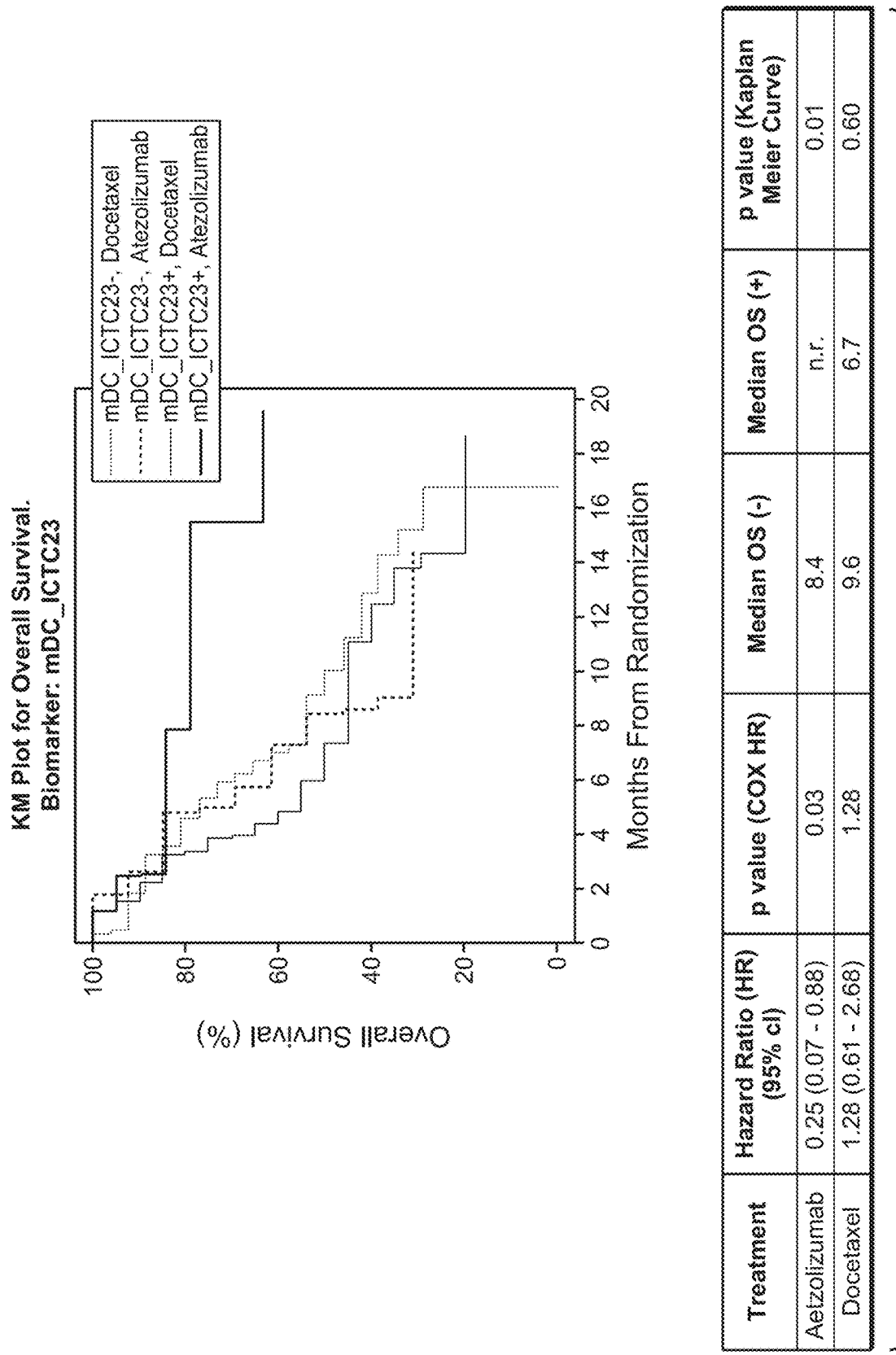
FIG. 12 shows that DC-related gene signature correlates with survival in PD-L1$^+$ patients with NSCLC treated with atezolizumab.

DC-related gene signature correlates with survival in patients treated with atezolizumab as shown in the Kaplan-Meier survival curves based on the expression of a cumulative DC gene signature including genes: XCR1, IRF8, FLT3, and BATF3 (FIG. 11). A higher DC signature score correlates with clinical benefit to a PD-1 axis inhibitor atezolizumab in patients with NSCLC (HR=0.54, p=0.04). The medium OS between patients with higher expression versus lower/no expression were separated by 7.9 months (8.5 vs 16.4). DC-related gene signature correlates with survival in PD-L1[+] patients treated with atezolizumab as shown in the Kaplan-Meier survival curves based on the expression of a cumulative DC gene score in patients who are positive for PD-L1 (FIG. 12). Included in the cumulative DC gene score are XCR1, IRF8, FLT3, and BATF3. PD-L1 expression was assessed prospectively on tumor cells and tumor-infiltrating immune cells with the VENTANA SP142 PD-L1 immunohistochemistry assay (Ventana Medical Systems, Tucson, Ariz., USA) (Fehrenbacher L, et. Al., Lancet 2016). Expressing of PD-L1 was scored as a percentage of total tumor cells and tumor-infiltrating immune cells expressing PD-L1 as a percentage of tumor area (tumor cells scored as percentage of PD-L1-expressing tumor cells: TC3≥50%, TC2≥5% and ≤50%, TC1≥1% and ≤5%, and TC0≤1%; tumor-infiltrating immune cells scored as percentage of tumor area: IC3≥50%, IC2≥5% and ≤50%, IC1≥1% and ≤5%, and IC0≤1%). We considered PD-L1+ patients grouped as TC3, TC2, IC3, and IC2. A strong correlation of DC signature score and clinical benefit to a PD-1 axis inhibitor atezolizumab was observed in PD-L1$^+$ patients (HR=0.25, p=0.03). The medium OS in patients with higher DC gene score was not reached, whereas in patients with lower/no expression has median OS of 8.4 months. In contrast, there is no correlation of DC genes expression to survival in PD-L1$^+$ patients received docetaxel.

---

The invention claimed is:

1. A method for treating a patient with NSCLC, the method comprising:
   (i) determining in vitro a DC-related gene signature expression level in a tumor tissue sample obtained from the patient, wherein the DC-related gene signature expression level is characterized by an expression level of a group of genes consisting of XCR1, IRF8, BATF3 and FLT3;
   (ii) comparing the DC-related gene signature expression level to a reference DC-related gene signature expression level that is a median DC-related gene signature expression level from a population of NSCLC patients, and
   (iii) if the DC-related gene expression level is above the reference DC-related gene signature expression level, treating the patient with a therapy comprising an effective amount of atezolizumab, wherein the tumor tissue sample is obtained from the patient before the therapy.

2. The method of claim 1, wherein the DC-related gene signature expression level is determined in the sample by RNA sequencing.

3. The method of claim 1, wherein the patient is a PD-L1+patient.

* * * * *

SEQUENCE LISTING

```
<160> NUMBER OF SEQ ID NOS: 10

<210> SEQ ID NO 1
<211> LENGTH: 10
<212> TYPE: PRT
<213> ORGANISM: Artificial Sequence
<220> FEATURE:
<223> OTHER INFORMATION: HVR-H1

<400> SEQUENCE: 1

Gly Phe Thr Phe Ser Asp Ser Trp Ile His
1               5                   10

<210> SEQ ID NO 2
<211> LENGTH: 18
<212> TYPE: PRT
<213> ORGANISM: Artificial Sequence
<220> FEATURE:
<223> OTHER INFORMATION: HVR-H2

<400> SEQUENCE: 2

Ala Trp Ile Ser Pro Tyr Gly Gly Ser Thr Tyr Tyr Ala Asp Ser Val
1               5                   10                  15

Lys Gly

<210> SEQ ID NO 3
<211> LENGTH: 9
<212> TYPE: PRT
<213> ORGANISM: Artificial Sequence
<220> FEATURE:
<223> OTHER INFORMATION: HVR-H3

<400> SEQUENCE: 3

Arg His Trp Pro Gly Gly Phe Asp Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: HVR-L1

<400> SEQUENCE: 4

Arg Ala Ser Gln Asp Val Ser Thr Ala Val Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: HVR-L2

<400> SEQUENCE: 5
```

Ser Ala Ser Phe Leu Tyr Ser
1               5

<210> SEQ ID NO 6
<211> LENGTH: 9
<212> TYPE: PRT
<213> ORGANISM: Artificial Sequence
<220> FEATURE:
<223> OTHER INFORMATION: HVR-L3

<400> SEQUENCE: 6

Gln Gln Tyr Leu Tyr His Pro Ala Thr
1               5

<210> SEQ ID NO 7
<211> LENGTH: 118
<212> TYPE: PRT
<213> ORGANISM: Artificial Sequence
<220> FEATURE:
<223> OTHER INFORMATION: VH

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 8
<211> LENGTH: 108
<212> TYPE: PRT
<213> ORGANISM: Artificial Sequence
<220> FEATURE:
<223> OTHER INFORMATION: VL

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg

<210> SEQ ID NO 9
<211> LENGTH: 447
<212> TYPE: PRT
<213> ORGANISM: Artificial Sequence
<220> FEATURE:
<223> OTHER INFORMATION: HC

<400> SEQUENCE: 9

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
```

```
                355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly
            435                 440                 445

<210> SEQ ID NO 10
<211> LENGTH: 214
<212> TYPE: PRT
<213> ORGANISM: Artificial Sequence
<220> FEATURE:
<223> OTHER INFORMATION: LC

<400> SEQUENCE: 10

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Ser Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Leu Tyr His Pro Ala
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```